(12) United States Patent
Xiao

(10) Patent No.: US 12,415,061 B2
(45) Date of Patent: Sep. 16, 2025

(54) NEEDLE ASSEMBLY FOR TATTOO DEVICE

(71) Applicant: Long Xiao, North York (CA)

(72) Inventor: Long Xiao, North York (CA)

(*) Notice: Subject to any disclaimer, the term of this patent is extended or adjusted under 35 U.S.C. 154(b) by 259 days.

(21) Appl. No.: 18/315,143

(22) Filed: May 10, 2023

(65) Prior Publication Data

US 2023/0364403 A1    Nov. 16, 2023

(30) Foreign Application Priority Data

May 12, 2022   (CN) .......................... 202210515820.9

(51) Int. Cl.
*A61M 37/00* (2006.01)

(52) U.S. Cl.
CPC .............................. *A61M 37/0076* (2013.01)

(58) Field of Classification Search
CPC ......... A61M 37/0076–0084; A61M 2205/106; A61M 5/3298; A61M 5/46; A61M 5/3234; A61M 5/322; A01K 11/005; A61B 17/205; A61B 2017/00769; A61B 10/0233

See application file for complete search history.

(56) References Cited

U.S. PATENT DOCUMENTS

| 768,413 | A | 8/1904 | Wagner | |
|---|---|---|---|---|
| 6,505,530 | B2 | 1/2003 | Adler et al. | |
| 7,380,480 | B1* | 6/2008 | Chen | A61M 37/0076 81/9.22 |
| 10,806,915 | B2 | 10/2020 | Xiao | |
| 11,040,185 | B2 | 6/2021 | Johansson | |
| 11,052,232 | B2 | 7/2021 | Xiao | |
| 2006/0020283 | A1 | 1/2006 | Lisec | |
| 2012/0192681 | A1* | 8/2012 | Klebs | A61M 37/0076 81/9.22 |
| 2013/0226211 | A1 | 8/2013 | Xiao | |
| 2015/0151098 | A1* | 6/2015 | Spendlove | A61M 37/00 606/186 |
| 2017/0157382 | A1* | 6/2017 | Siciliano | A61M 37/0076 |

(Continued)

FOREIGN PATENT DOCUMENTS

| CA | 3011593 A1 | 1/2020 |
|---|---|---|
| CN | 201595866 U | 10/2010 |

(Continued)

OTHER PUBLICATIONS

Extended European Search Report dated Oct. 19, 2023 in related European Patent Application No. 23171460 (4 pages).

*Primary Examiner* — Brigid K Byrd

(57) ABSTRACT

A tattoo needle assembly has a housing comprising a longitudinal channel, a needle bundle mounted in the longitudinal channel and reciprocally movable between a retracted position and an extended position, and a biasing member engaged with the housing and the needle bundle for biasing the needle bundle at least radially to an inner wall of the housing. The housing comprises first and second guide surfaces forming a V-shaped guideway on the inner wall. The needle bundle comprises first and second sliding surfaces for slidably engaging the guideway. The biasing member radially biases the needle bundle to slidably engage the guideway such that the guide surfaces of the guideway and the sliding surfaces of the needle bundle form a V-V sliding pair during reciprocal movement of the needle bundle between the retracted position and the extended position.

20 Claims, 16 Drawing Sheets

(56) References Cited

U.S. PATENT DOCUMENTS

| 2019/0209823 | A1 | 7/2019 | Veil et al. |
| 2019/0217072 | A1 | 7/2019 | Xiao |
| 2020/0023175 | A1 | 1/2020 | Xiao |
| 2020/0390980 | A1 | 12/2020 | Neumetzler |
| 2022/0143378 | A1 | 5/2022 | Xiao |
| 2022/0184365 | A1* | 6/2022 | Grimmelbein .... A61M 37/0076 |
| 2023/0270986 | A1 | 8/2023 | Xiao |

FOREIGN PATENT DOCUMENTS

| CN | 106902452 A | 6/2017 |
| CN | 110404159 A | 11/2019 |
| EP | 3995171 A2 | 5/2022 |

* cited by examiner

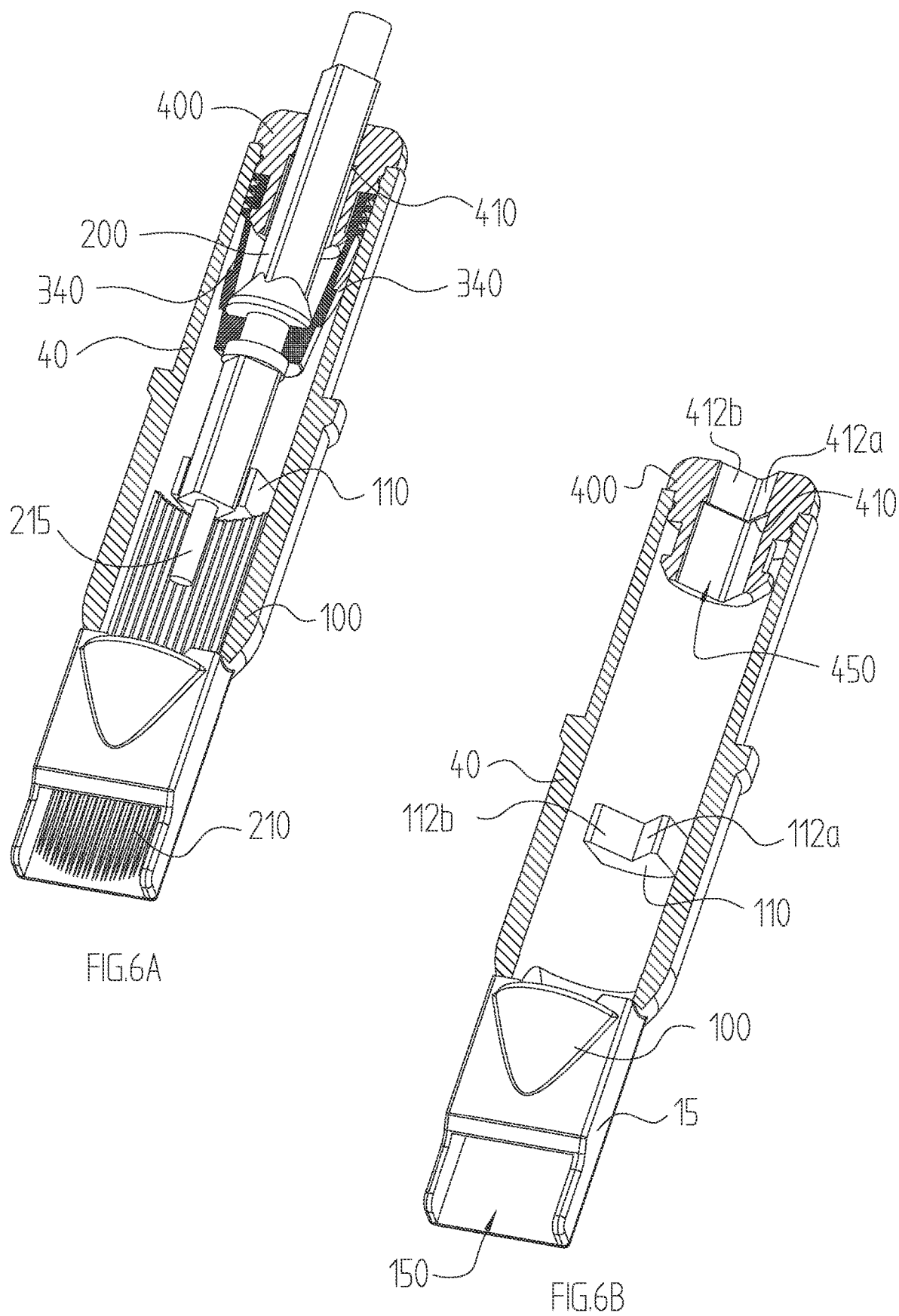

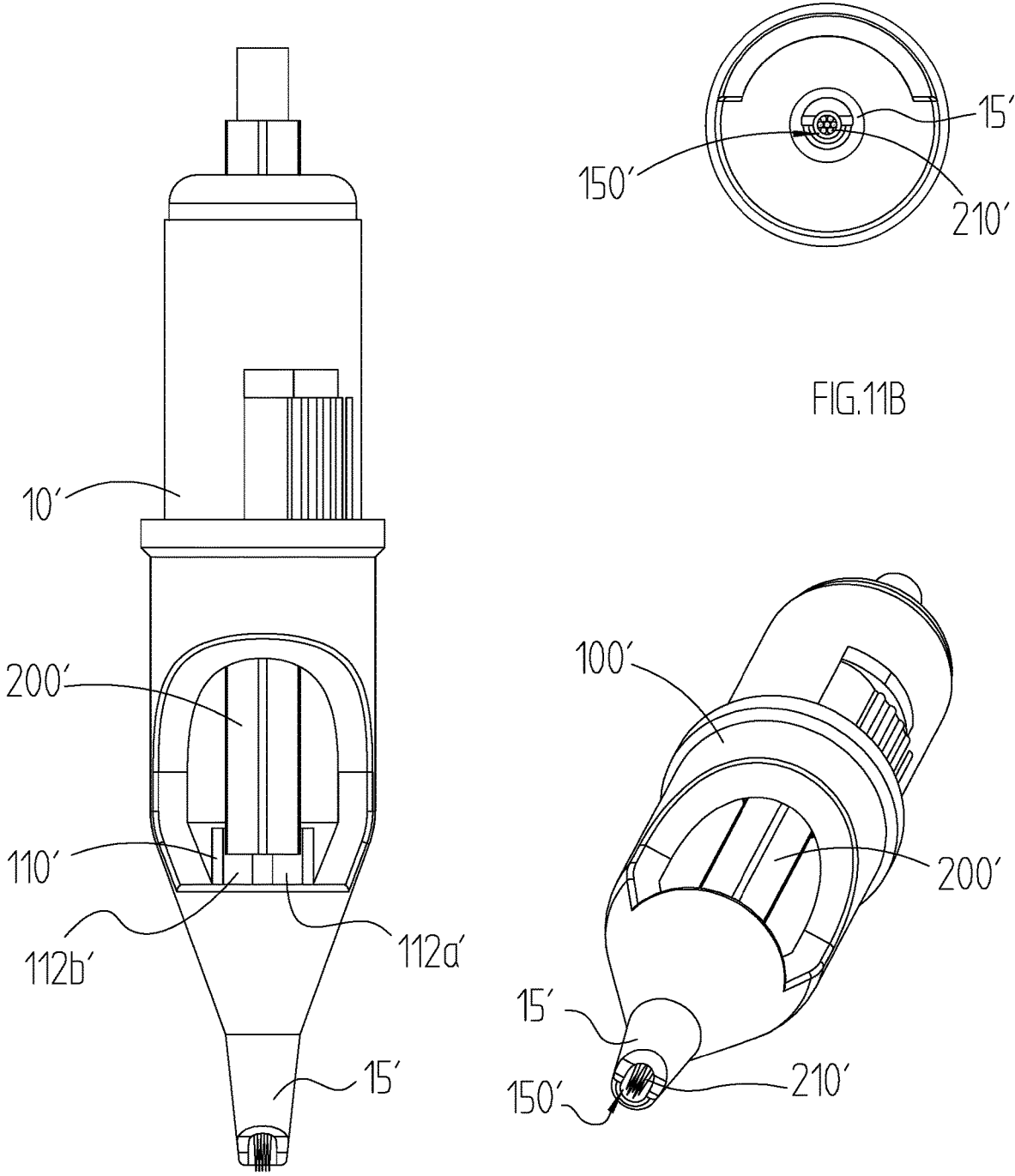

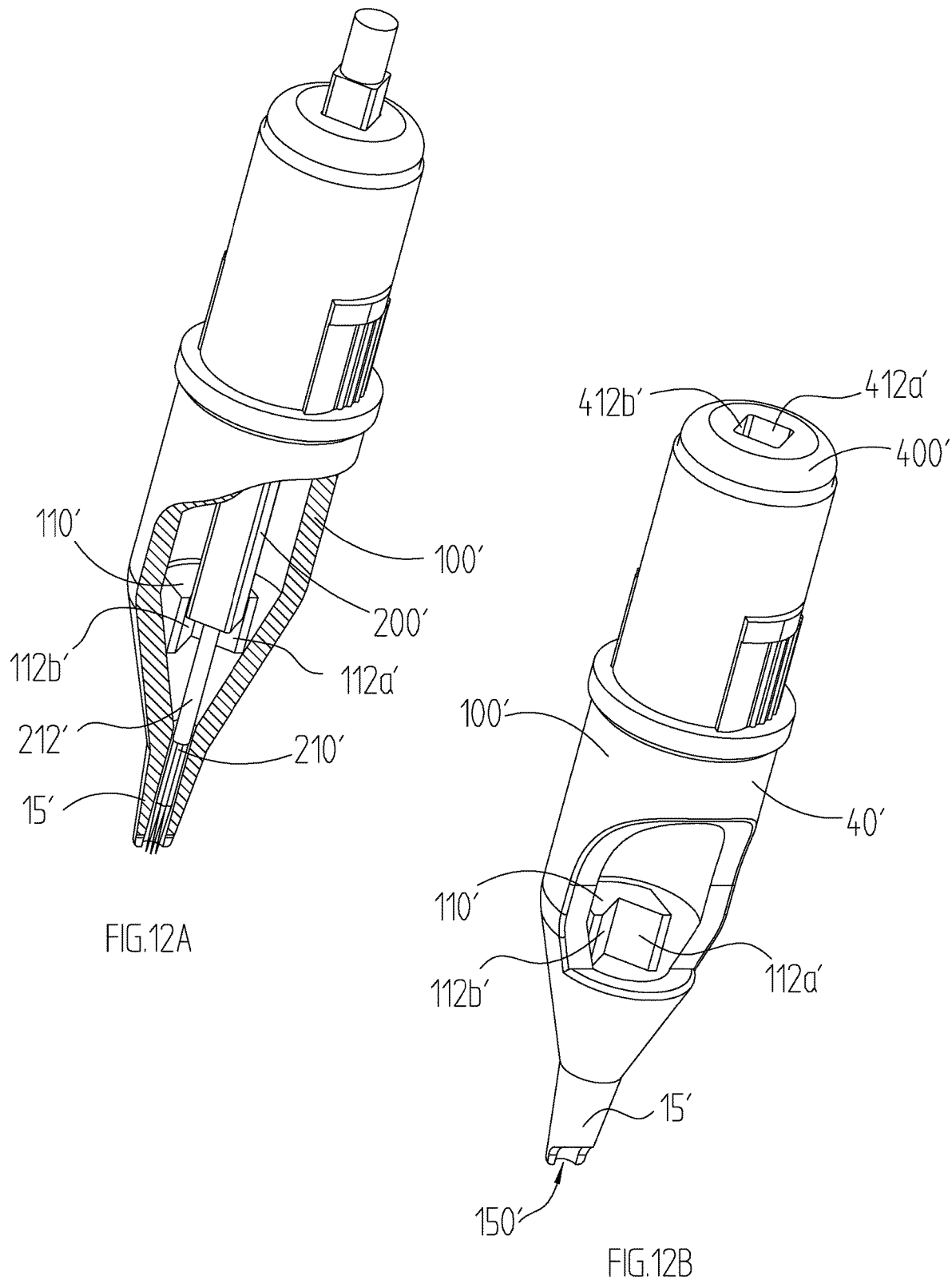

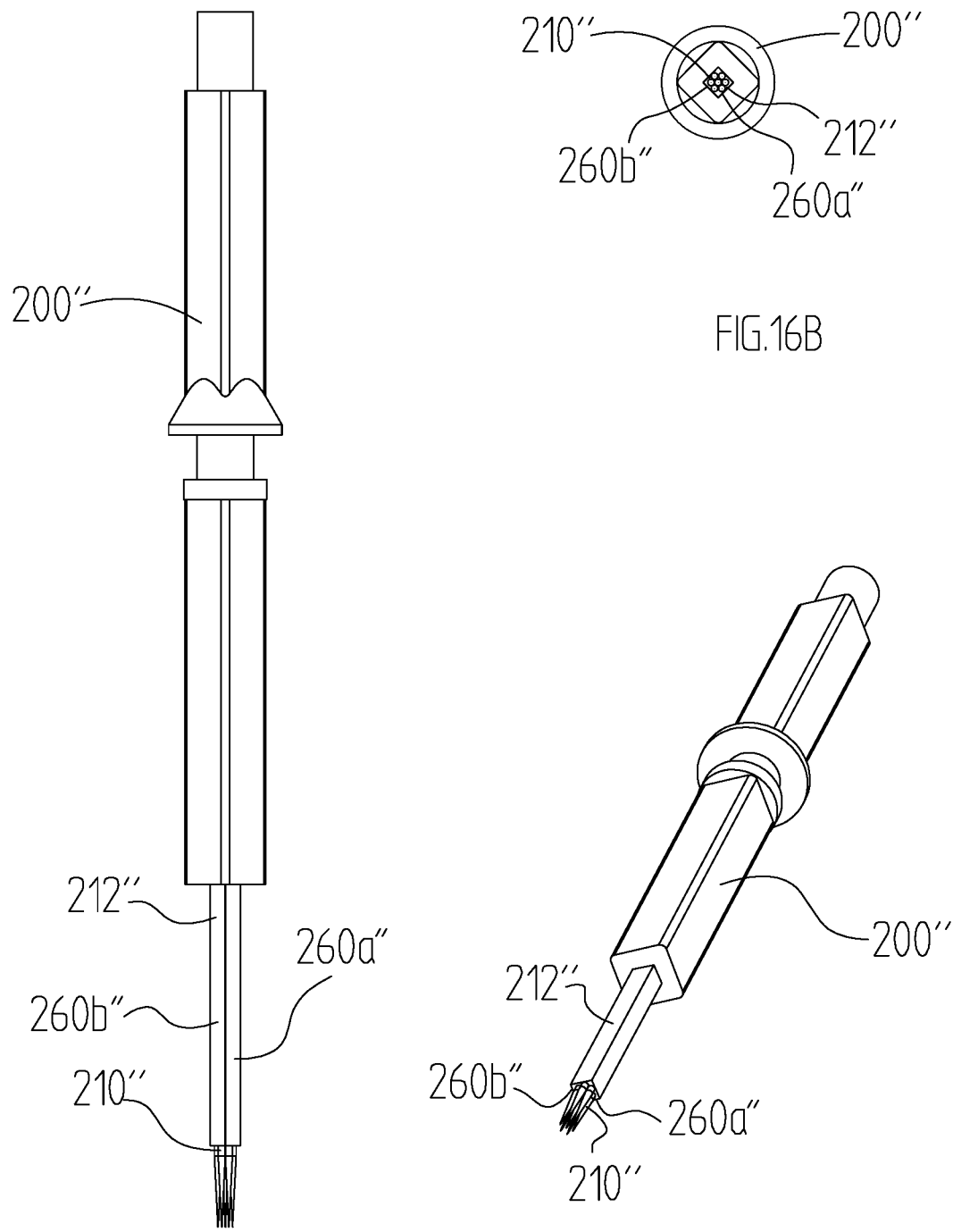

NEEDLE ASSEMBLY FOR TATTOO DEVICE

CROSS-REFERENCE TO RELATED APPLICATIONS

The present application claims the benefit of and priority to Chinese Patent Application No. 202210515820.9, filed May 12, 2022, the entire contents of which are incorporated herein by reference.

FIELD

The present invention relates generally to devices for tattooing or permanent makeup, in particular to a needle assembly for a tattoo device.

BACKGROUND

A tattoo device typically includes a tattoo needle for applying ink to the skin, a tattoo machine with a tattoo needle actuator, and a handle connecting the tattoo needle to the tattoo machine, which can be conveniently held in the operator's hand to manipulate the tattoo needle during use. During operation, the tattoo needle actuator drives the tattoo needle to reciprocatively extend and retract, thereby repeatedly piercing the skin of the person being tattooed. The tattoo needle(s) may be provided in a removable needle assembly that is attachable to the handle. The needle assembly is usually sterilized before use and is disposed and replaced after each session, so it is convenient to use a replaceable and disposable needle assembly.

The needle assembly is typically an assembly of a bundle of tattoo needles (referred to as "needle bundle") and a suitable casing, which are pre-assembled into one unit. A tattoo needle assembly may also be referred to as a needle cartridge or needle module.

A conventional needle assembly usually has a needle casing (housing) for mounting a needle bundle therein. The casing includes a longitudinal channel between an upper end and a lower open end. A tattooist usually holds and uses the tattoo device (typically the handle) like holding and using a pen for writing during tattoo operations, such that the tips of the needles are directed downward. The needle casing has a lower open end, commonly referred to as the mouthpiece, to allow the needles to pass through and contact the skin to be tattooed. The upper part of the needle casing is configured to engage the needle handle, usually by a quick connect-and-lock mechanism such as a bayonet connection.

The needle bundle is movably mounted in the longitudinal channel of the needle casing for reciprocating movement between a retracted position and an extended position. The needle bundle includes a bar or rod and a set of needles attached to the bar or rod. The needle bundle is normally in the retracted position and the needle tip portion is fully enclosed by the casing. During use, the needle bundle is driven by the actuator to the extended position, where the tip portion of the needles extend out of the mouthpiece and can therefore contact the skin to be tattooed.

Typically, when the drive shaft of the actuator pulls back, it does not pull the needle bundle back with it. Thus, some conventional tattoo needle assemblies also include an elastic and resilient biasing member for applying a longitudinal force to pull the needle bundle back to the retracked position from the extended position during each stroke. A biasing member can also be configured to apply a lateral/radial force to push the tip portion of the needle bundle towards one side of the inner wall of the casing, such as against a side of the opening in the mouthpiece to stabilize and guide the needles during operation.

For example, U.S. Pat. No. 6,505,530, published 14 Jan. 2003, disclosed an ink application device; and U.S. Pat. No. 11,040,185, published 22 Jun. 2021 disclosed a disposable tattoo needle cartridge.

Example tattoo devices and needle assemblies are also disclosed in CN201595866U issued 6 Oct. 2010, US2019/0217072 published 18 Jul. 2019, and US2020/0023175 published 23 Jan. 2020.

Needle bundles are typically sold with manufacturer-stated nominal sizes, but the actual cross-sectional size of each needle bundle can still vary. In order to accommodate needle bundles with varied sizes, the opening in the mouthpiece is typically sized such that a gap is provided between the needle bundle and the casing in many conventional needle assemblies. This gap allows the needle bundle to reciprocate at a high speed (such as 100 to 150 stroke/second or up to 170 stroke/second, with typical stroke lengths of 2 mm to 5 mm without too much friction or jamming, and to draw tattoo ink with the needles through the mouth opening. However, a drawback the gap is that the needle tips can wobble in a radial direction in the gap. When the needle tips wobble, it is difficult to precisely position the needle tips on the skin for tattooing, such as to draw a thin line or a small dot.

An add-on tattoo needle stabilization device has been disclosed in US2012/0192681, published 2 Aug. 2012, which can be snapped on a sanitary tube of a traditional tattoo machine to engage the shaft of the needle on the tattoo machine in a cradle of the stabilization device, which biases the tip of the needle against the inside edge of the tip aperture of the sanitary tube. However, the needle tip portion in such a device can still wobble, and also rotate about the needle axis during operation. Rotation of the needle tip portion of a flat or magnum needle is undesirable as such rotation can result in unintended cuts in the skin and unintended tattoo effects.

It is thus desirable to provide improved tattoo needle assemblies having multiple needles in the needle bundle with reduced needle tip wobbling and rotation.

SUMMARY

An aspect of the present disclosure is to provide a stabilizer in a tattoo needle assembly for stabilizing the needle bundle during longitudinal reciprocal movement, where the stabilizer restricts both lateral and rotational movements of the needle bundle, and can accommodate different needle bundles with various sizes and shapes. The stabilizer may include a V-shaped guideway or a V-V sliding pair.

In one aspect, there is provided a needle assembly for a tattoo device comprising a housing comprising a longitudinal channel; a needle bundle mounted in the longitudinal channel and reciprocally movable between a retracted position and an extended position; a biasing member engaged with the housing and the needle bundle for biasing the needle bundle at least radially to an inner wall of the housing. The housing comprises a pair of first and second guide surfaces forming a V-shaped guideway on the inner wall; and the needle bundle comprises a corresponding pair of first and second sliding surfaces for slidably engaging the guideway. The biasing member is configured to radially bias the needle bundle to slidably engage the guideway such that the guide surfaces of the guideway and the sliding surfaces of the needle bundle form a V-V sliding pair during reciprocal movement of the needle bundle between the retracted position and the extended position.

In another aspect, there is provided a needle assembly for a tattoo device, comprising a housing comprising a longitudinal channel and a V-shaped guideway extending longitudinally in the longitudinal channel; a needle bundle mounted in the longitudinal channel and reciprocally movable between a retracted position and an extended position, the needle bundle comprising a V-shaped slider for slidably engaging the guideway; and a biasing member for radially biasing the needle bundle to slidably engage the guideway during movement of the needle bundle between the retracted and extended positions. The guideway and the slider may form a V-V sliding pair. The guideway may be concave V-shaped and the slider may be convex V-shaped, or the guideway may be convex V-shaped and the slider may be concave V-shaped.

A needle assembly described herein may include one or any combination of the following features. The guide surfaces and sliding surfaces are parallel to a longitudinal movement direction of the needle bundle. The housing may comprise a front end and a rear end, the front end comprising a mouthpiece having a mouth opening, the longitudinal channel extending from the front end to the rear end. The V-V sliding pair may be located adjacent to or in the mouthpiece. The housing and the needle bundle may be configured to form one or more further sliding pairs, a first one of the one more further sliding pairs being located adjacent to or at the rear end of the housing. The first further sliding pair may comprise a further V-V sliding pair. The housing may comprise a cap at the rear end of the housing, the cap comprising a bore having a pair of third and fourth guide surfaces forming a further V-shaped guideway in the cap, and the needle bundle may comprise a corresponding pair of third and fourth sliding surfaces adjacent to the cap for slidably engaging the further V-shaped guideway in the cap to form the further V-V sliding pair. The mouthpiece may comprise the pair of the first and second guide surfaces. The housing may comprise a M-shaped member on the inner wall, the M-shaped member comprising the pair of first and second guide surfaces. The needle bundle may comprise a needle shaft and a set of needles attached to the needle shaft, and the needle shaft may comprise the sliding surfaces. The needle bundle may comprise a needle shaft and a set of needles soldered together by a solder bar attached to the needle shaft, and the solder bar comprises the pair of the first and second sliding surfaces. The biasing member may be further configured to apply a longitudinal force to longitudinally bias the needle bundle from the extended position towards the retracted position. At least one of the guide surfaces and the sliding surfaces may be lubricated by a lubricant or have a lubricated coating. At least one of the pair of the first and second guide surfaces and the pair of the first and second sliding surfaces may comprise polyoxymethylene or polytetrafluoroethylene to reduce surface friction. The pair of the first and second guide surfaces, or their respective extension planes, may intersect at an angle of 60 to 120 degrees. The needle bundle may comprise a neck for engaging a front end of the biasing member. At least one sliding pair may be provided between the neck and a front end of the needle bundle and at least one sliding pair may be provided between the neck and a rear end of the needle bundle. The biasing member may be oriented to generate a radial biasing force directed generally towards an intersection of the first and second guide surfaces.

Other aspects, features, and embodiments of the present disclosure will become apparent to those of ordinary skill in the art upon review of the following description of specific embodiments in conjunction with the accompanying figures.

BRIEF DESCRIPTION OF THE DRAWINGS

In the figures, which illustrate, by way of example only, embodiments of the present disclosure:

FIG. 6A is another partially-cutaway perspective view of the needle assembly of FIG. 1, with both the housing and the needle bundle;

FIG. 6B is a partially-cutaway perspective view of the housing of the needle assembly of FIG. 6A without the needle bundle;

FIGS. 11A, 11B, and 11C are side, bottom, perspective views, respectively, of a needle assembly for a round needle, according to another embodiment of the present invention;

FIG. 12A is a (partially-cross-sectional) perspective view of the needle assembly of FIG. 11A;

FIG. 12B is a perspective view of the housing of the needle assembly of FIG. 11A;

FIGS. 16A, 16B, 16C are front, bottom, and perspective views, respectively, of the needle bundle of the needle assembly of FIG. 14A;

DETAILED DESCRIPTION

Figure 1:
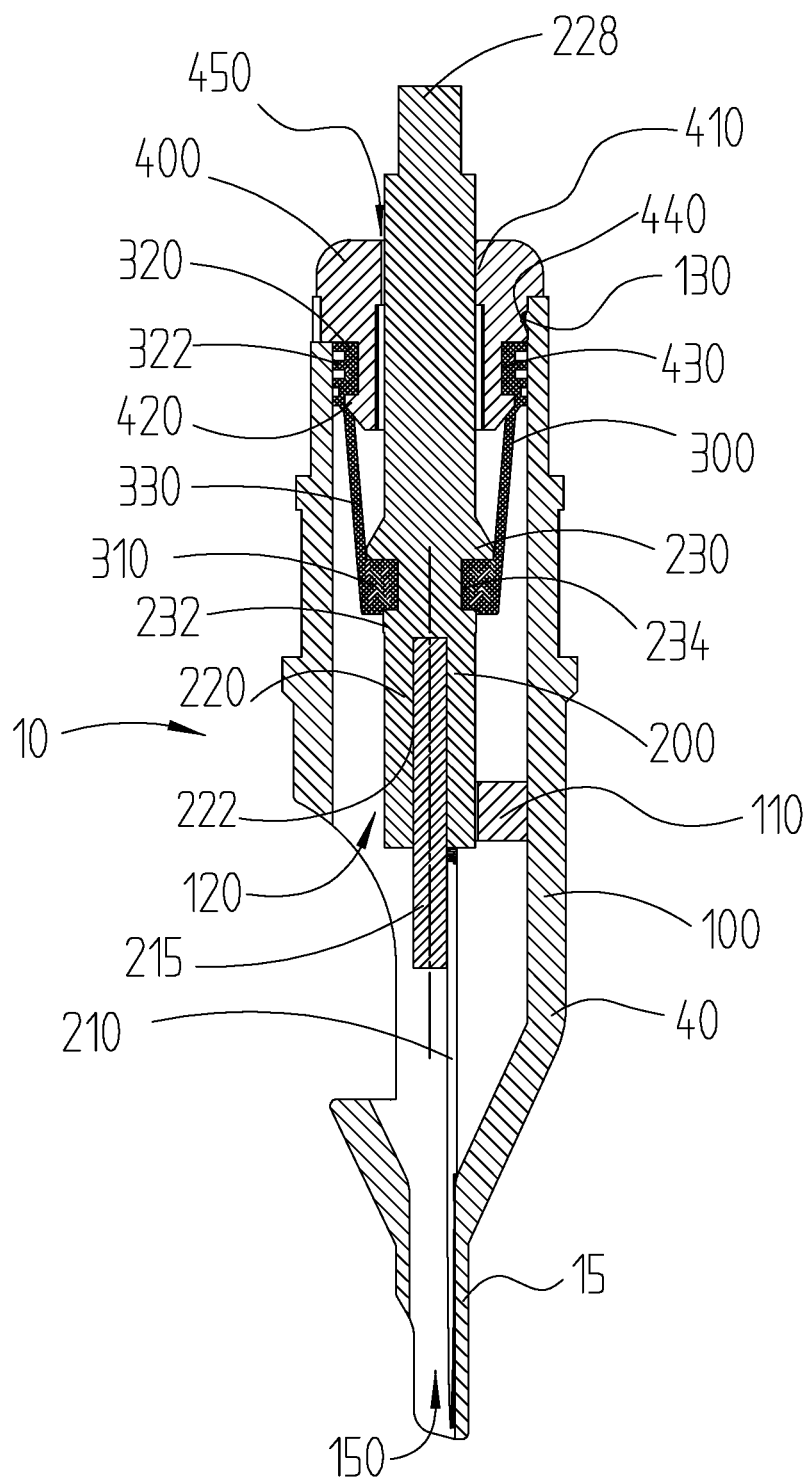
FIG. 1 is a cross-sectional view of a needle assembly for a flat needle, according to an embodiment of the present disclosure.
Figure 2A:
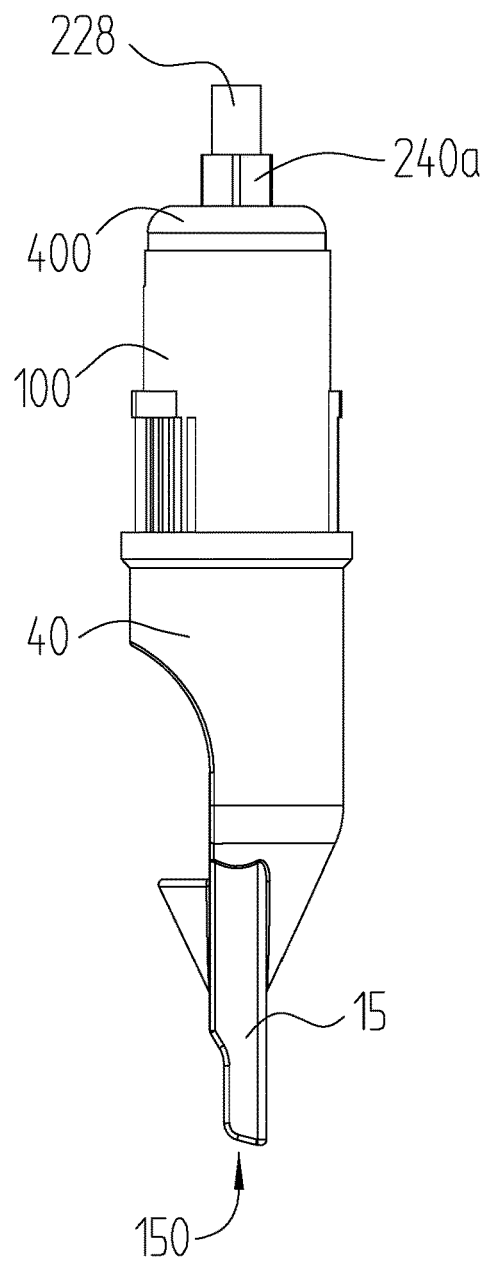
FIGS. 2A, 2B, and 2C are front, side, and top views, respectively, of the needle assembly of FIG. 1, respectively.
Figure 2B:
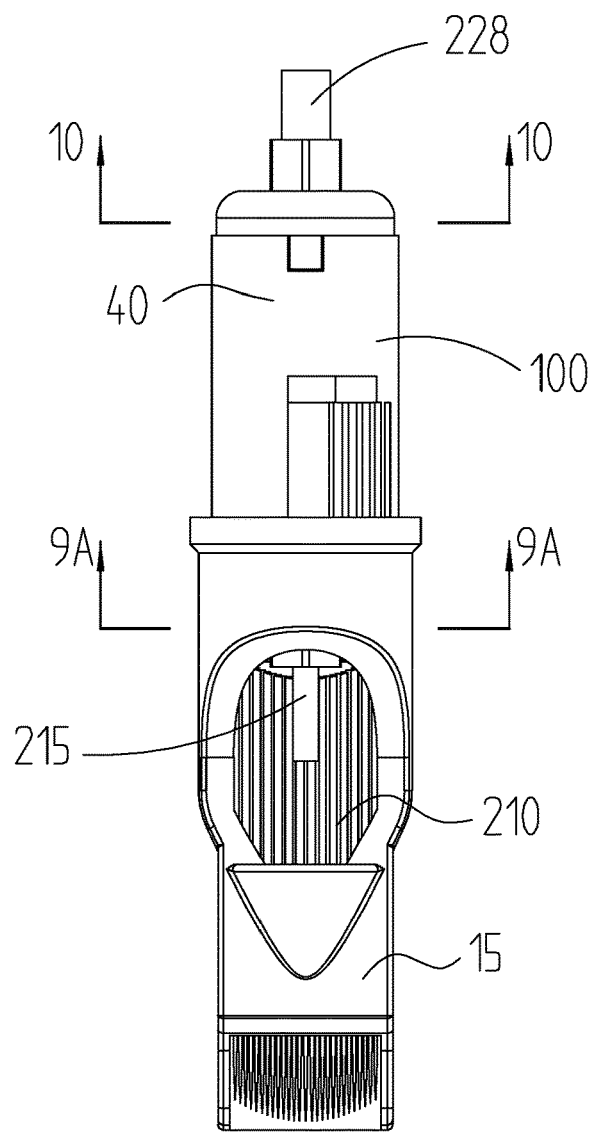
Figure 2C:
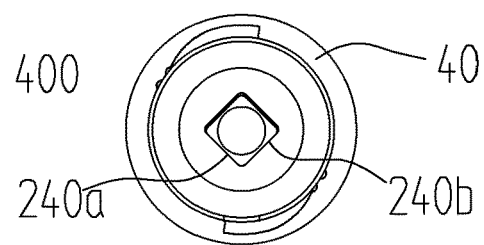

In brief overview, in an embodiment, a V-V sliding pair is provided in the housing of a needle assembly for stabilizing the movement of the needle bundle and reducing wobbling and rotation of the needle tips.

The sliding pair may be formed by a generally V-, M-, Y-, or W-shaped stabilizer or guideway on the inner wall of the housing and a correspondingly shaped slider on the needle bundle. As used herein, the "V-V" sliding pair may have a generally V-V, M-V, V-\/, M-\/, Y-V, Y-\/, \/-\/, /\-/\, W-/\, /\-/\, W-/\, or /\-/\ configuration. For ease of reference, all of these forms of configuration are included in the expression "V-V sliding pair", or "V-shaped" guideway or coupling and other terms referring to the "V-shape" (unless otherwise specified). In different embodiments, the stabilizer and the slider may be provided in different forms.

The coupling or engagement of the sliding pair can be maintained or secured by a biasing member in the needle assembly, which may be a biasing member known to those skilled in the art, that applies a lateral force to the needle bundle to press the slider of the needle bundle against the stabilizer. To reduce friction, a lubricant may be applied or coated on one or both of the guide surfaces of the stabilizer and the sliding surfaces of the slider in some embodiments. In different embodiments, multiple, such as two or three sliding pairs may be provided to guide and improve stable movement of the needle bundle.

Conveniently, the V-V sliding pair as described herein allows longitudinal reciprocal movement of the needle bundle at high speeds, and stably supports the needle bundle and reduces or prevents wobbling of the needle tips during operation. Consequently, the needle tips can be more precisely positioned for tattoo operations.

In addition, with the V-V sliding pair, a gap can be maintained between the needle tips and the mouth opening in some embodiments such that the needle tips do not contact the mouth opening at the extended position.

The V-V sliding pair as described herein can thus address one or more problems or drawbacks of conventional needle assemblies including conventional needle modules and cartridges, such as the problem of needle wobbling during tattoo operation. The V-V sliding pair as described herein can provide more stable and more precise tattoo operations, even as compared to conventional needle assemblies equipped with a biasing member or stabilizing device where the biasing member or stabilizing device applies a lateral force to press the needle bundle against a smoothly curved inner wall of the needle casing or the stabilizing device, such as a circular or semicircular surface at the mouth opening or inside the needle casing.

In particular, it has been recognized that when bundled needles are pressed against a flat or smoothly curved wall, two radially opposing forces are applied to the needle bundle and the needle tips can still move sideways or circumferentially along the flat or smoothly curved circular or semicircular wall surface, and thus will still wobble during high-speed operation. It is particularly problematic when the needle bundles include a set of multiple needles and have different cross-sectional shapes and sizes, or when the needle shaft or the needle set has a larger cross-sectional curvature than the curvature of the guiding surface or the supporting surface in the cradle of a stabilization device, which can occur quite often because the shapes and sizes of the needle bundles, even those with the same manufacturer-stated sizes, can vary significantly for various reasons as discussed elsewhere herein.

By comparison, a V-V sliding pair pressed by a radial biasing force provides two separate and symmetrical reactive forces on the needle bundle that are angled and opposing each other circumferentially/laterally. As a result, the needle bundle is subjected to three balanced forces in the radial and circumferential directions, which can conveniently restrict not only radial movement but also lateral and circumferential movement of the needles and can thus further reduce or eliminate wobbling and improve stability of the needles during operation. The V-V sliding pair can also provide increased contact area between the guideway and the needle bundle, which further improves stability of the needle bundle. Conveniently, the reactive forces can also prevent rotation of the needle tip portion during operation.

The V-V sliding pair is formed by a V-shaped guideway in the needle housing and a V-shaped slider provided on the needle bundle. The V-shaped guideway has a pair of guide surfaces configured and oriented to apply two reactive lateral forces on the needle bundle, where the reactive lateral forces are symmetrical relative to the line (radial direction) of the radial force applied on the needle bundle by a biasing member so that the two reactive lateral forces not only provide a net reactive radial force that counterbalances the radial force applied by the biasing member to radially stabilize the needle bundle in the radial direction, but also counterbalance each other for stabilizing the needle bundle in the lateral/circumferential direction. The slider on the needle bundle has a corresponding pair of sliding surfaces configured and oriented to slidably engage the guideway. The sliding surfaces of the slider form a V-shape corresponding to the V-shape of guideway, and the sliding surfaces and guide surfaces are in close area contact and slidably engaged during operation. The V-shaped guideway and the V-shaped slider also conveniently prevent rotation of the needle tip portion.

FIGS. 1 to 4 illustrate an embodiment of a tattoo needle assembly 10, which can also be referred to as a tattoo needle module or tattoo needle cartridge.

As can be appreciated by those skilled in the art, needle assembly 10 can be attached to a tattoo machine (not shown) such as through a tattoo handle (not shown). It is noted that needle assembly 10, and other embodiments of needle assemblies to be described below, may be configured to couple to and used with any suitable tattoo machines or tattoo needle handles, including conventional tattoo machines, as can be readily appreciated by those skilled in the art after reviewing this disclosure. For example, example tattoo machines, devices and handles are disclosed in U.S. Ser. No. 11/052,232, U.S. Ser. No. 10/806,915, and US2019/0217072, the entire contents of each of which are incorporated herein by reference. Thus, except for aspects or features described below, other details of such suitable tattoo machines and tattoo handles and their operation that are not the focus of, or not particularly relevant to, the present disclosure will not be described herein for the purpose of brevity.

The needle assembly 10 includes a needle housing 40, a needle bundle 200, and a biasing member 300.

The needle housing 40 includes a body portion 100 with a mouthpiece 15 at the front end (the lower end, as depicted in FIG. 1) of the body portion 100, and a cap 400 mounted at the rear end (the upper end, as depicted in FIG. 1) of the body portion 100.

The needle housing 40, particularly the body portion 100 including the mouthpiece 15, and the cap 400 can be made of a plastic material, such as polycarbonate.

The body portion 100 has a longitudinal channel 120 extending from the rear end to the front end. As depicted the front end of the body portion 100 includes the mouthpiece 15, and the rear end of the body portion 100 is an open end and includes an annular protrusion 130 on its inner wall. The protrusion 130 may be configured to function as a male bayonet connector 130 for engaging the cap 400 as will be further described below.

As depicted, the mouthpiece 15 is integrally formed with the body portion 100 and has an opening 150 that allows the needle tips of the needle bundle 200 to pass therethrough. Opening 150 is also referred to as the mouth opening herein.

In different embodiments, the mouthpiece 15 and the body portion 100 may be separately provided as two separate pieces and are attached to each other.

As depicted in FIG. 1, it may be considered that the mouth opening 150 is the lower open end of the needle housing 40.

The needle housing 40 also includes a stabilizer formed of one or more generally M-shaped supporting and guiding members fixedly or removably mounted therein.

Figure 3:
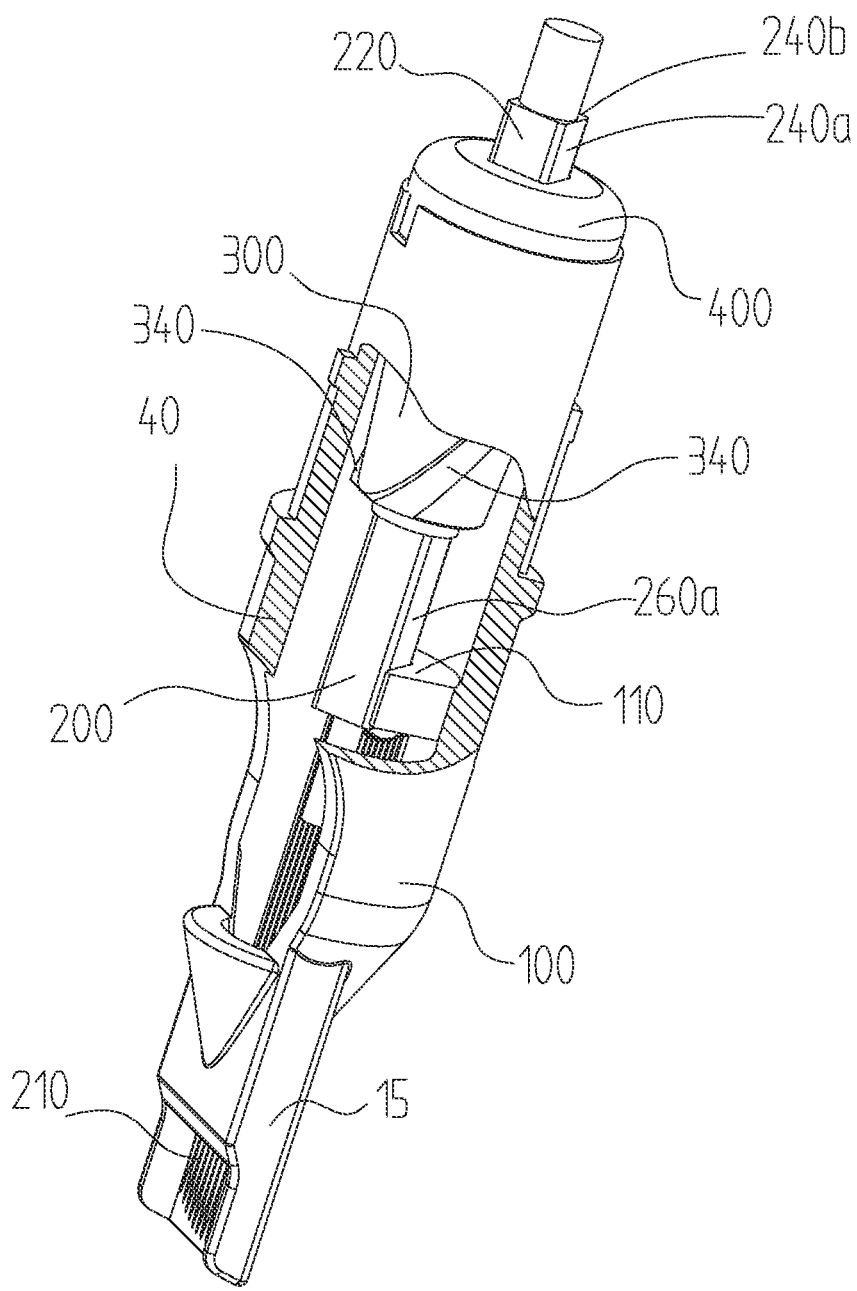
FIG. 3 is a partially-cutaway perspective view of the needle assembly of FIG. 1.
Figure 4:
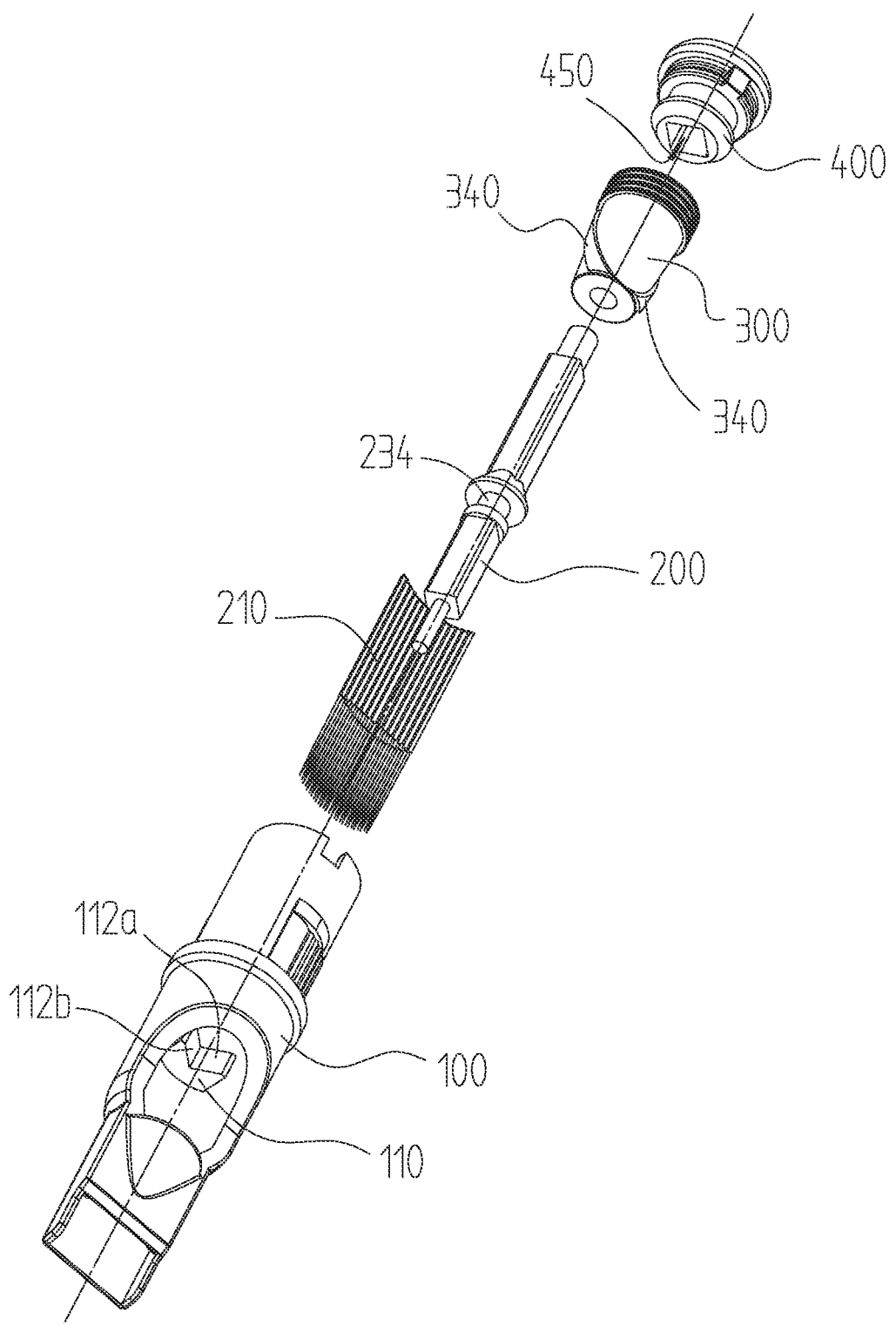
FIG. 4 is an exploded view of the needle assembly of FIG. 1.

As depicted in FIGS. 1 and 3, a lower supporting and guiding member 110 is provided at middle section of the body portion 100. The member 110 may be integrally formed on body portion 100 or may be separately formed and mounted inside the body portion 100 by any suitable technique, such as being glued, bonded, fastened, welded, or the like. The member 110 has a generally M-shaped cross-section as can be better seen in FIGS. 6A, 6B and 9A (and may be referred to as "the M-shaped member" hereinafter). As will be further described below, the M-shaped member 110 may be located at a longitudinal position in the longitudinal channel 120 corresponding to the point where a lateral biasing force is to be applied by the biasing member 300. The M-shaped member 110 is positioned on the side of the body portion 100 towards which the needle bundle 200 is biased by the biasing member 300. That is, the lateral biasing force applied by the biasing member 300 when it is stretched is in the direction towards the M-shaped member 110.

The M-shaped member 10 has two guide surfaces 112a, 112b (also individually or collectively referred to as guide surfaces 112), which are configured and used to support and guide the needle bundle 200 during use as will be further explained below. The surfaces 112a and 112b are each flat and they intersect at an angle of about 90 degrees as depicted, to form a generally V-shaped guideway.

The cap 400 is separately formed and is plugged into the rear open end of the body portion 100 to engage the body portion 100 through a quick connection. As depicted, the cap 400 has a central opening (through hole) 450 and an annular groove 440, which is shaped and sized to match and engage the protrusion 130 on body portion 100. The groove 440 may be configured to function as a female bayonet connector. The quick connection between the body portion 100 and the cap 440 may thus be a bayonet connect formed by the protrusion 130 on the body portion 100 and the corresponding groove 440 on the cap 400. One or more bayonet connectors may be provided in different embodiments. The body portion 100 and cap 400 are detachably engaged by the bayonet connection to form the needle housing 40. The longitudinal channel 120 connects the mouth opening 150 and the central opening 450 of the cap 400 when the cap 400 is mounted on body portion 100. The cap 400 with opening 450 may be considered the upper open end of the needle housing 40.

As better illustrated in FIGS. 6A to 8D, an upper or rear portion of the cap 400 is configured and shaped to provide an upper supporting and guiding member 410 in the central opening 450, which has two intersecting guide surfaces 412a, 412b (also individually or collectively referred to as guide surfaces 412) that form a generally V-shaped guideway (the member 410 is thus referred to hereinafter as the "V-shaped member"). Guide surfaces 412a and 412b may also intersect at an angle of about 90 degrees. The V-shaped member 410 may be integrally formed with cap 400 or may be separately provided and mounted on cap 400, similar to mounting M-shaped member 110 in the body portion 100 as described above.

FIGS. 6A and 6B better illustrate both the M-shaped member 110 and the V-shaped member 410. As can be seen, the M-shaped member 110 is closer to the mouth opening 150 at the lower (front) end of the needle housing 10, and the V-shaped member 410 is closer to the upper end opening 450 of the needle housing 10.

The integrally formed body portion 100 with member 110, and cap 400 with member 410, may be formed by injection molding from a plastic material.

The members 110 and 410 may also be separately formed from a plastic material and then bonded or welded, such as by ultrasonic welding, to the body portion 100 or cap 40, respectively.

As illustrated in FIGS. 8A, 8B, 8C, 8D, the cap 400 has a through bore 450 that allows the rear end 228 of the needle shaft 220 to move reciprocally therein. The rear end 228 of the needle shaft 220 can be contacted and driven by the drive shaft (not shown) of the tattoo machine (not shown) to in turn drive needle bundle 200 to move downward.

Some conventional (traditional) needle assemblies include a cap similar to cap 400, but the central bore in the cap is typically cylindrical, and the corresponding needle shafts of conventional needle bundles are cylindrical. In order to ensure smooth high-speed reciprocating movement of the needle shaft in the bore, the size of the bore in the cap is slightly larger than the rear end of the needle shaft, so a gap is provided between the cap and the needle shaft, and the gap is sufficiently large to accommodate varying sizes of the replaceable needle bundles.

As shown in FIG. 1, the needle bundle 200 includes a needle rod (or bar) 215 and a set of needles, referred to as needle set 210 attached to the needle rod 215, as in a conventional needle bundle. However, in distinction from a conventional needle bundle, the needle bundle 200 has a needle shaft 220 connected to the needle rod 215 that is specially designed and constructed to engage and couple with the M-shaped member 110 and V-shaped member 410.

In particular, as illustrated in FIGS. 3 and 7A to 7C, the needle shaft 220 has generally V-shaped sliding surfaces for coupling with the members 110, 410 to form respective sliding pairs. Specifically, a front section of the needle shaft 220 is provided with sliding surfaces 260a and 260b (also individually or collectively referred to as sliding surfaces 260), and a rear section of the needle shaft 220 is provided with sliding surfaces 240a and 240b (also individually or collectively referred to as sliding surfaces 240). Sliding surfaces 260 are configured for slidingly engagement and coupling with the guide surfaces 112 to form a lower (front) V-V sliding pair. Sliding surfaces 240 are configured for slidingly engagement and coupling with the guide surfaces 412 to form an upper (rear end) V-V sliding pair.

In other words, the needle bundle 200 includes a lower (front) slider portion providing sliding surfaces 260 for forming a V-V sliding pair with the M-shaped member 110, and an upper (rear) slider portion providing sliding surfaces 412 for forming a V-V sliding pair with the V-shaped member 410.

The slider portions may be formed in any suitable manner. In a particular embodiment, the slider portions may be formed using a solder material as further described below.

As in a conventional needle assembly, the needle bundle 200 is movably mounted and guided in the longitudinal channel 120 of the needle housing 40 in a manner that allows the needle bundle 200 to reciprocate up and down during use, between a retracted position and an extended position. In the extended position, the tip portion of the needle set 210 can extend through the mouth opening 150 to puncture the skin and apply tattoo ink to the skin. In the embodiment depicted in FIG. 1, the rear end 228 of the needle bundle 200 protrudes from the rear end of the needle housing 40, through the opening 450 of the cap 400, such that the rear end 228 can be contacted and driven by a driving shaft of the tattoo machine, as in a conventional tattoo machine.

In the embodiment described above and illustrated in the drawings, the generally square-shaped bore 450 and the corresponding square-shaped rear end 228 of the needle shaft 220 conveniently orient the needle bundle 200 and prevents rotation of the needle shaft 220, with the benefit that the sliders on the needle shaft 220 can be correctly oriented to face and be coupled with the stabilizers such as M-shaped member 110 and V-shaped member 410. A gap may still exist (the rear end 228 and the bore 450 are not closely fit) so longitudinal movement of the needle bundle 200 is not hindered at the cap 400.

In various embodiments, each or at last one of the guide surfaces and sliding surfaces may be lubricated by a lubricant or have a lubricated coating to facilitate sliding movement and reduce frictional resistance to the sliding motion. For example, the lubricant may be a Vaseline™ or similar materials. The lubricant should be safe and compatible to the skin in case some of the lubricant material may be unintentionally spread to the needle tips. For example, a known medical-grade lubricant may be used. The lubricant can reduce friction, and the heat generated by friction, and can reduce vibration during sliding movement so as to further stabilizing the tip portion of the needle bundle.

In different embodiments, the guide and sliding surfaces may be formed of a self-lubricating material. For example, in some embodiments, one or more of the guide surfaces and sliding surfaces may be formed of a material containing polyoxymethylene (POM), polytetrafluoroethylene (PTFE), graphite, or silicone to reduce surface friction, such as a PTFE plastic material. For example, the M-shaped member 110, the V-shaped member 410, and the needle shaft 220 may be formed of the self-lubricating material, such as materials that contain a suitable content of POM, PTFE, silicone, graphite, or the like. The contact surfaces on the M-shaped member 110, the V-shaped member 410, and the needle shaft 220 may also be coated with a suitable lubricant material, which may be a liquid or solid lubricant.

Needle set 210 may include any number of needles arranged in an array or a formation, as in a conventional needle set.

As is known to those skilled in the art, the formation of a conventional needle set typically has a generally or substantially circular (round) or rectangular (flattened or magnum) cross-sectional profile.

Conventional needle sets commonly available include "round needles" typically formed of 1-18 individual needles in a generally round profile. Round needles include round linear (RL) needles or round shader (RS) needles. When the number of needles in the needle set is higher, such as 4-27 needles, the needles are formed in a generally flattened or rectangular profile, known as "flat needles" (single row) and "magnum needles" (two rows). For example, commonly available flat needles include F series (single-row linear) flat needles. Magnum needles include M1 series (double-row weaved) magnum needles, and RM series (round magnum) needles (also known as curved magnum needles, or CM needles).

Regardless of their formation, the tattoo needles are typically formed of stainless steel.

The number and size of the needles may be selected based on the desired tattooing effect by the operator or user. Different sizes, numbers of needles, and formations of the needles may be selected and used for different reasons and purposes. Needles of standard sizes may be used. The diameter of an individual needle may be 0.25 mm, 0.30 mm, or 0.35 mm in some embodiments. The design and construction of the needle set itself is not the focus of the present disclosure and will not be further discussed herein.

However, the different types (shapes) and sizes of the needle sets can affect how the needle bundle 200 works in a needle assembly as described herein.

For example, it should be understood that the length of the V-shaped guideway, or the longitudinal length of each sliding surface on the needle bundle 200, or both, should be sufficiently long and relatively positioned to ensure that the V-V sliding pair remains engaged during the entire stroke of the needle bundle. For example, if the stroke length of the needle bundle is 3 mm, the V-shaped sliding pair formed by the guideway and the sliding surfaces is configured to allow the needle bundle to slide on the guideway for sliding distance of about 3 mm or more. The V-shaped sliding pair may provide a sliding distance of 2 mm to 5 mm in some embodiments.

As another example, as illustrated in FIG. 7, when the needle set 210 is an RM needle set, which includes 27 needles forming a substantially rectangular (magnum) cross-sectional profile and a curved tip profile. As such, the mouth opening 150 is configured to have a corresponding rectangular shape to better accommodate the needle set 210.

In an embodiment, the connecting rod 215 may be formed of a stainless steel and may have a cylindrical shape. The needles in the needle set 210 may be soldered together with a solder material and attached to the connecting rod 215 with the same or a different solder material. The connecting rod 215 may be attached to the needle shaft 220 by insertion into a rod bore 222 at the front end of the needle shaft 220. The connecting rod 215 and the needle shaft 220 may be bonded or coupled together to form the needle bundle 200. The connecting rod 215 may be considered a part of the needle shaft 220, and the sliding surfaces may be formed on the connecting rod 215 in some embodiments.

Figure 5:
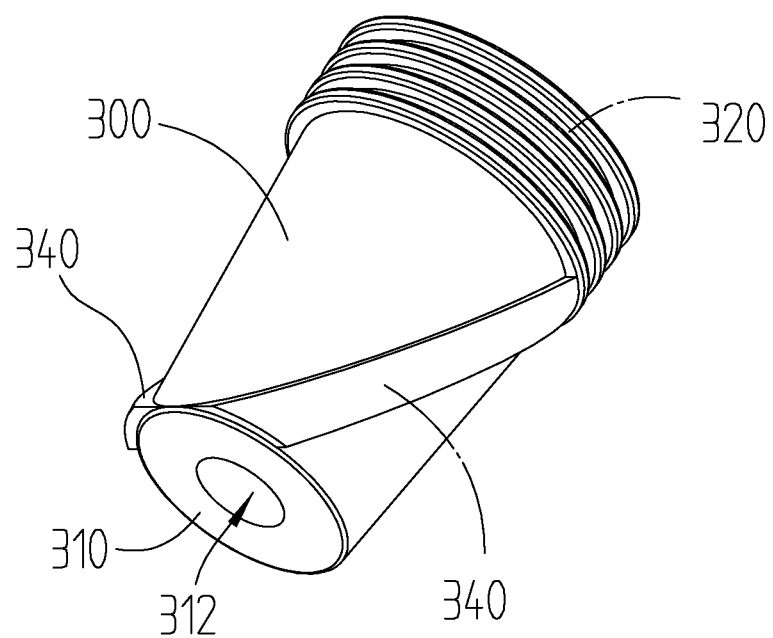
FIG. 5 is a perspective view of a biasing member of the needle assembly of FIG. 1.
Figure 7A:
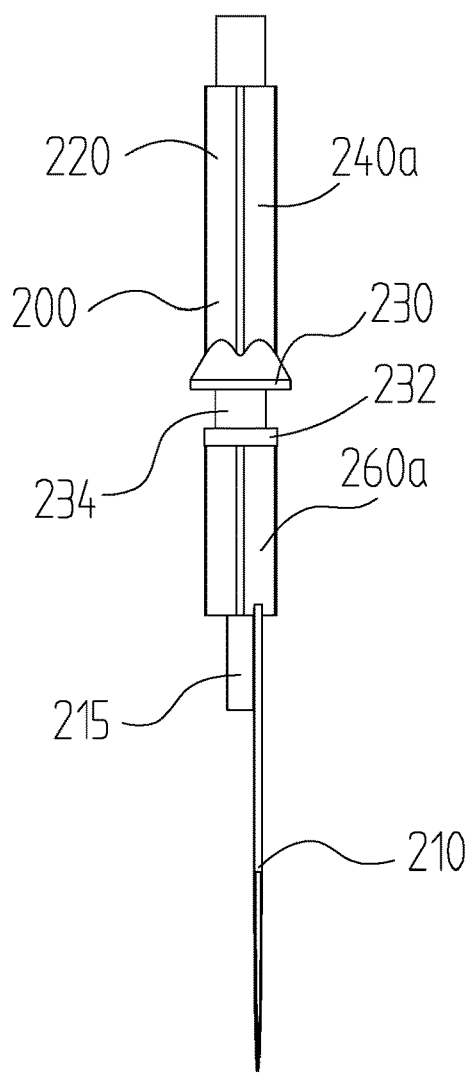
FIGS. 7A, 7B, and 7C are front, side, and perspective views, respectively, of the needle bundle of the needle assembly of FIG. 1, respectively.
Figure 7B:
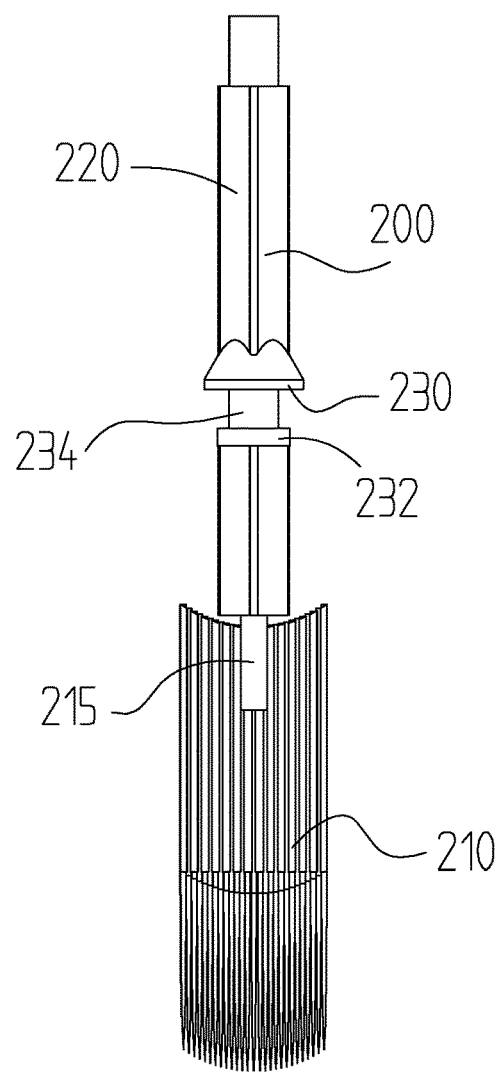
Figure 7C:
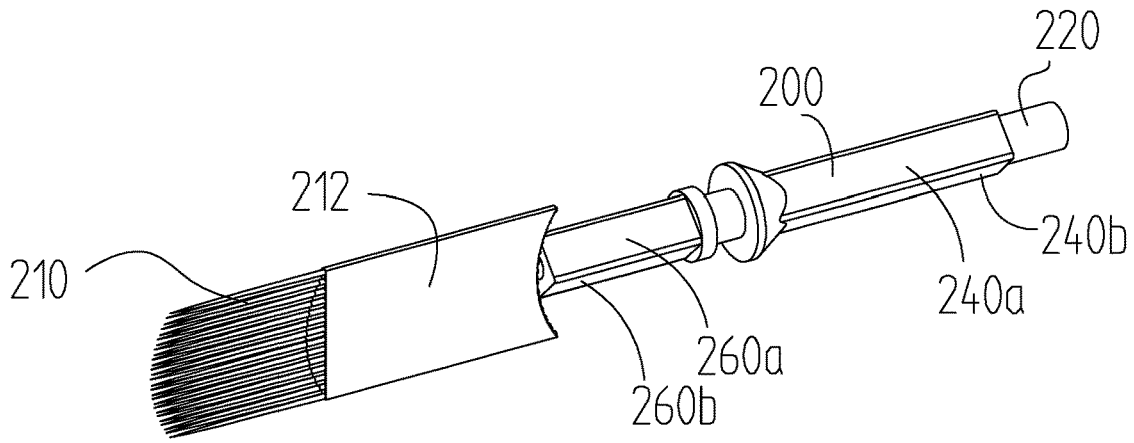
Figure 8A:
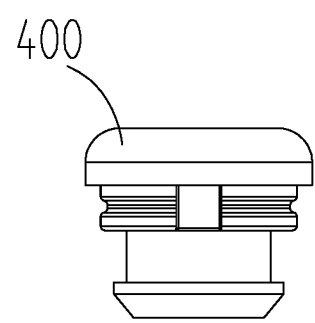
FIGS. 8A, 8B, 8C, and 8D are front, cross-sectional, top, and perspective views, respectively, of the cap of the needle assembly of FIG. 1, respectively.
Figure 8B:
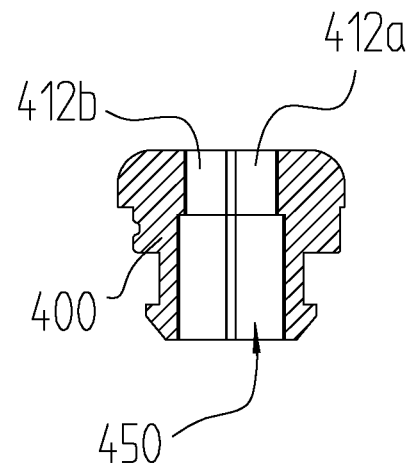
Figure 8C:
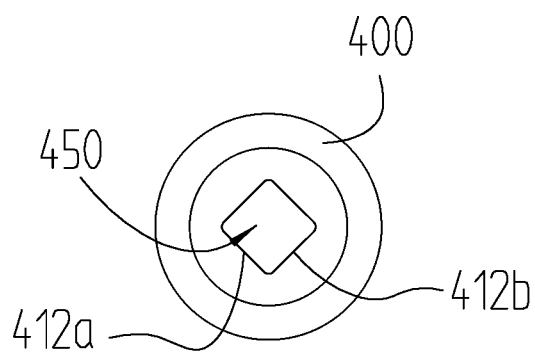
Figure 8D:
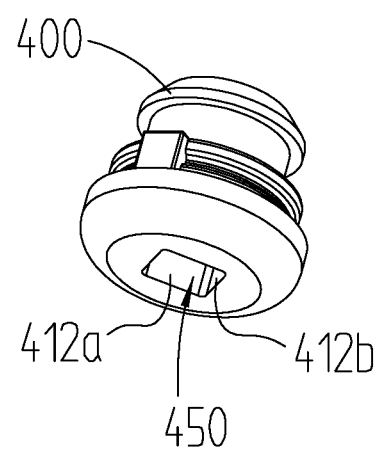

In some embodiments, as illustrated in FIGS. 1, 5 and 6A, needle shaft 220 may have a shoulder 230, a collar 232, and a neck 234 for engaging the lower end 310 of the biasing member 300, as will be further explained below.

Typically, the drive shaft on a conventional tattoo machine (not shown) abuts the rear end of the needle shaft to apply only a downward driving force but cannot engage the needle shaft to apply an upward force on the needle bundle to pull the needle bundle back from the extended position to the retracted position. Thus, a biasing member is needed to pull the needle bundle back to the retracted position so the needle bundle can reciprocate repeatedly.

Accordingly, as illustrated in FIGS. 1 and 5, a tubular resilient biasing member 300 is provided in the needle assembly 10 to enable and facilitate the reciprocal longitudinal movement of the needle bundle 200. Further, the biasing member 300 is configured to press the needle bundle 200 radially towards the stabilizer, such as the M-shaped member 110, as will be further described below.

The biasing member 300 includes a lower end 310, an upper end 320, and a tubular (barrel-shaped) elastic stretchable portion 330 connecting the lower end 310 and the upper end 320. Inclined tension ribs 340 are arranged on the outer surface of the elastic stretchable portion 330, so that, when the elastic portion 300 is stretched, the ribs 340 produce a radial or lateral biasing force to press the needle bundle 200 toward the M-shaped member 110. The lower end 310 is connected to the needle bundle 200 as will be described below. The shape and size of the upper end 320 closely match (fit) the inner wall of the body portion 100 to engage the inner wall of the body portion 100. Therefore, the upper end portion 320 is fixedly mounted in the needle housing 40.

The lower end portion 310 of the biasing member 300 is configured to sealingly engage the needle shaft 220 of needle bundle 200. The opening 312 in the lower end portion 310 is sized and shaped such that the needle shaft 220 forms a close fit with the lower end portion 310 at the opening 312, so as to form a fluid-tight seal between the biasing member 300 and the needle bundle 200, while at the same time allowing the shaft 220 to axially move up and down during operation without breaking the seal.

As depicted, the lower end portion 310 has a thickened section with an upward facing surface, and the shoulder 230 engages the upward facing surface of the lower end portion 310. The thickened section of the lower end portion 310 is sized and shaped to closely couple with the shoulder 230, such that shoulder 230 exerts a downward force on the thickened section of the lower end portion 310 to pull the lower end portion 310 down when the needle bundle 200 is driven to move towards the extended position. As the lower end portion 310 is pulled downward, the biasing member 300 is stretched and the length of the biasing member 300 increases. As a result, the biasing member 300 produces a longitudinal biasing force to bias the needle bundle 200 upward. After the needle bundle 200 reaches the final extended position, the longitudinal biasing force applied by the biasing member 300 pulls the needle bundle 200 back up to the retracted position.

The biasing member 300 not only facilitates the reciprocal movement of the needle bundle 200, but the inclined tension ribs 340 also urge and press the needle bundle 200 radially toward the M-shaped member 110 on the needle housing 40 when the biasing member 300 is stretched. Thus, the biasing member 300 conveniently provides two biasing component forces with a simple construction.

The needle shaft 220 is inserted through the central opening 312 at the lower end 310, and the lower end 310 of the biasing member 300 tightly engages around the neck 234 of the needle shaft 220 to form a seal. The shoulder 230 and collar 232 engage the inner and outer wall surfaces of the lower end 310 adjacent the opening 312 respectively, so that the lower end 310 of the biasing member 300 is fixedly mounted at the neck 234 and will move with the needle shaft 220 when the needle bundle 200 reciprocates during operation. The collar 232 further limits the relative movement between the lower end portion 310 of the biasing member 300 and the needle bundle 200. The collar 232 is spaced from the shoulder 230 by the neck 234, so that the lower end portion 310 of the biasing member 300 is received in the groove formed by the shoulder 230, collar 232 and neck 234 to attach the lower end portion 310 to the needle bundle 200. Thus, the movement of the lower end portion 310 relative to the needle bundle 200 is limited and restricted by shoulder 230 and collar 232.

The biasing member 300 may be constructed in any suitable manner, such as similar to known biasing members, including those disclosed in, for example, CN201595866U, US2020/0023175, and US2019/0217072, the entire contents of each one of which are incorporated herein by reference. The biasing members disclosed in U.S. patent application Ser. No. 17/682,831 are also suitable, the entire contents of which are incorporated herein by reference.

Other suitable biasing members may also be used to replace biasing member 300 to provide both longitudinal and lateral/radial biasing forces. Suitable biasing members may be provided in the form an elastic band, elastic ring, an elastic tubing, or the like.

Biasing member 300 may be formed from any suitable material having suitable strength and resiliency. Further, the biasing member 300 can be replaced by other biasing mechanisms, such as an O-ring and a hook. Other biasing devices known to those skilled in the art may be used as long as they provide the required biasing forces to pull the needle bundle 200 back and urge the needle bundle 200 towards the guide surfaces. In some embodiments, separate biasing members may be used to provide longitudinal and radial biasing forces, respectively.

Figure 9A:
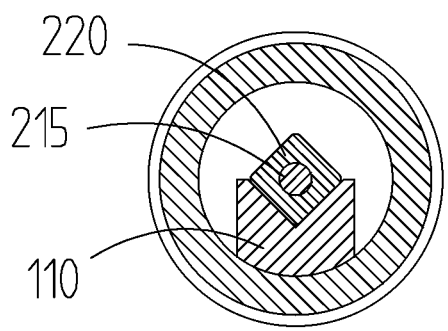
FIG. 9A is an axial cross-sectional view of the needle assembly of FIG. 1, along line 9A-9A in FIG. 2B.
Figure 10:
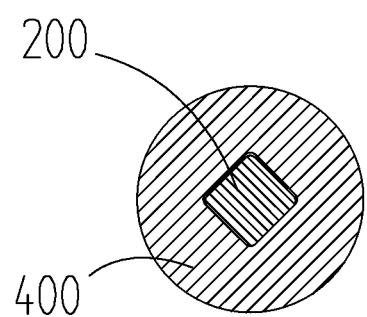
FIG. 10 is a cross-sectional view of the needle assembly of FIG. 1, along line 10-10 in FIG. 2B.

FIG. 9A shows a cross-sectional view of the lower/front sliding pair formed by the M-shaped member 110 and the lower/front slider on needle shaft 220. FIG. 10 shows a cross-sectional view of the upper/rear sliding pair formed by the V-shaped member on cap 400 and the upper/rear slider on needle bundle 200.

As can now be appreciated by those skilled in the art, the shapes, sizes, and intersecting angle between the intersecting surfaces in a V-V sliding pair may vary and still provide the desired effects of restricting radial and lateral movement of the needle shaft 220 and thus reducing wobbling.

For example, FIGS. 9B to 9F illustrate some embodiments of possible V-V sliding pair that are different from the embodiment shown in FIG. 9A.

Figure 9B:
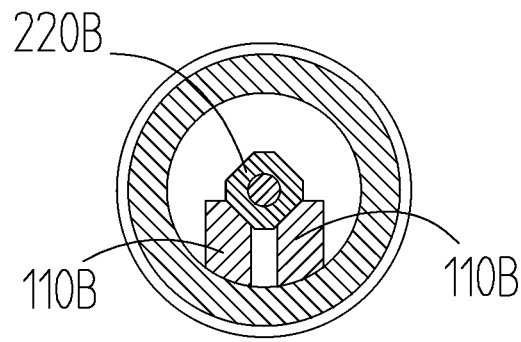
FIGS. 9B-9F are corresponding axial cross-sectional views of different needle assemblies, according to different embodiments of the present disclosure.

In particular, FIG. 9B illustrates that the M-shaped member may be replaced by two separate supporting and guiding members 110B. Each member 110B has a bevelled or chamfered top edge providing a guide surface. The two guide surfaces on the members 110B intersect in the sense that their extension planes intersect (at 90 degrees as depicted) even though the guiding surfaces are separated by a gap and are not continuous or connected. As can be understood, in another embodiment, the lower portions of the members 110B may be connected or integrally formed such that the two separate guiding surfaces are provided on a one-piece member. For clarity, it should be understood that two intersecting V-shaped surfaces include the situations in which the two surfaces form a "\ /"-shape or "/ \"-shape, as long as the extension planes of the two surfaces intersect and the intersection line is parallel to the axial direction of the needle shaft 220.

Similarly, the slider member on the needle shaft 220 may also have correspondingly different shapes and cross-sectional profiles. For example, the cross-sectional shape of the slider section or slider member on the needle shaft can be quadrilateral, pentagonal, or hexagonal, or have another suitable shape, as long as two intersecting sliding surfaces corresponding to the two guiding surfaces on the stabilizer are provided so a V-V sliding pair can be formed.

As depicted, the guiding surfaces form a concave V-shaped groove (valley guideway), so the sliding surfaces form a corresponding convex V-shaped slider. In some embodiments, the guiding surfaces may form a convex V-shaped guideway (ridges), in which case the sliding surfaces should form a corresponding concave V-shaped (groove or valley) slider. For example, a convex guideway may be provided by a generally W-shaped member. In any event, the guide surfaces (112 or 412) and sliding surfaces (260 or 240) are flat surfaces parallel to the axial/longitudinal direction of needle housing 40, along which the needle bundle 200 reciprocates, to form the V-V sliding pair.

As illustrated in FIG. 9B, a slider section of a needle shaft 220B may have an irregular octagonal shape, and the sliding surfaces of the slider may be separated by a transition section, regardless of whether the guiding surfaces are separated by a gap or not. Alternatively, the needle shaft 220 of FIG. 9A may also be used with the guiding members 110B shown in FIG. 9B.

Figure 9C:
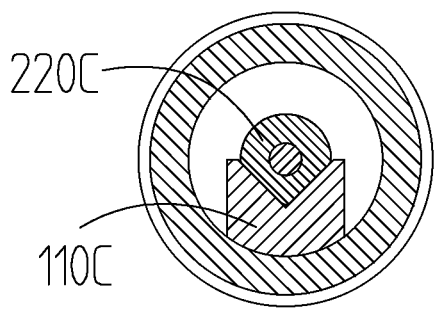

FIG. 9C shows another possible slider shape on a needle shaft 220C, which can be used with the M-shaped member 110C (or another guiding and supporting member such as member 110 or 110B). The slider section on the needle shaft 220C has two intersecting sliding surfaces as in needle shaft 220 but the top portion as depicted has an arched or semicircular shape. As can be understood, the non-contacting surface at the slider section may have any shape because this shape does not affect the function and operation of the sliding pair.

Figure 9D:
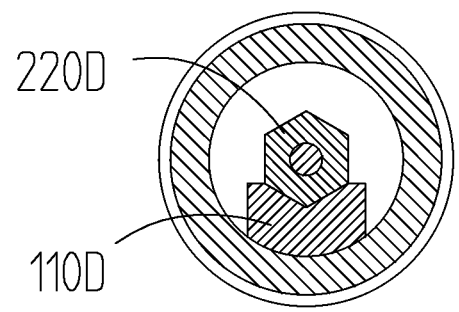

FIG. 9D illustrates a needle shaft 220D having a regular hexagonal cross-section, and the intersecting angle of the guiding/sliding surfaces is 120 degrees.

Figure 9E:
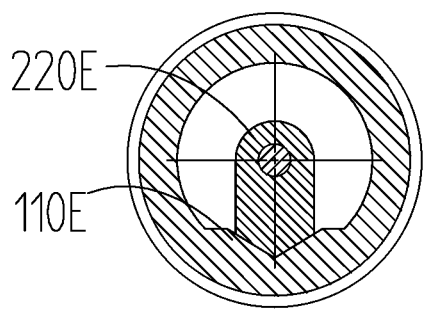

FIG. 9E illustrates an embodiment in which a stabilizer (guideway) 110E is integrally formed on the inner wall of the housing, with intersecting V-shaped guiding surfaces. The slider section on a needle shaft 220E has corresponding V-shaped sliding surfaces. The non-contacting (top) portion of the slider section is semicircular in cross-section.

Figure 9F:
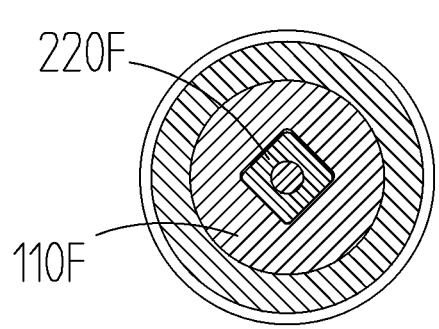

FIG. 9F illustrates a different embodiment in which a stabilizer 110F mounted on the housing has a generally square bore, and the correspondingly square-shaped slider section on a needle shaft 220F is received and enclosed in the bore.

As illustrated in FIGS. 9B, 9E, and 9F, a stabilizer in the needle housing 40 for providing a V-shaped sliding pair is not limited to a generally M-shaped member but may have a different configuration and general shape in different embodiments. As another example, the M-shaped member may also be replaced by a generally Y-shaped member (not shown) to provide the V-shaped guide surfaces or guideway. It should also be understood that a M-shaped member does not need to have strictly parallel sides beside the "V." For example, the M-shaped member may have a generally inverted-W shape.

In some embodiments, the needle shaft 220 may include a branched or extended rigid arm (not shown in FIG. 1) that provides the sliding surfaces to allow the M-shaped member 110 be positioned closer to the mouthpiece 15. The extended arm of the needle shaft 220 is parallel to the needle set 210 and may extend beyond the end of the needle bar 215 as depicted in FIG. 1 but does not contact the needle set 210. Because the arm is rigid, the arm can guide the movement of the needle set 210 when the arm slides on the M-shaped member 110. For instance, the needle shaft 220E illustrated in FIG. 9E may be modified to provide a branched or extended arm with a V-shaped slider in contact with the stabilizer (guideway) 110E, where the modified needle shaft may have a generally "=---" or "h" shape at the front end.

FIGS. 11A to 13C illustrate a different embodiment of the needle assembly, assembly 10'. The assembly 10' includes needle bundle 200' with a needle set 210' that is referred to as a round needle. The needle set 210' may include seven needles as depicted in FIG. 11B.

Similar to the needle assembly 10, the needle assembly 10' also includes a needle housing 40', which includes a body portion 100', a mouthpiece 15' at the lower/front end of the body portion 100', and a cap 400' at the rear/upper end of the body portion 100'. The mouthpiece 15' has a mouth opening 150'. An M-shaped stabilizer 110' is mounted in the needle housing 40', providing V-shaped intersecting guide surfaces 112a', 112b'. Similar to cap 400, the cap 400' also includes a stabilizer providing guide surfaces 412a', 412b'.

Figure 13A:
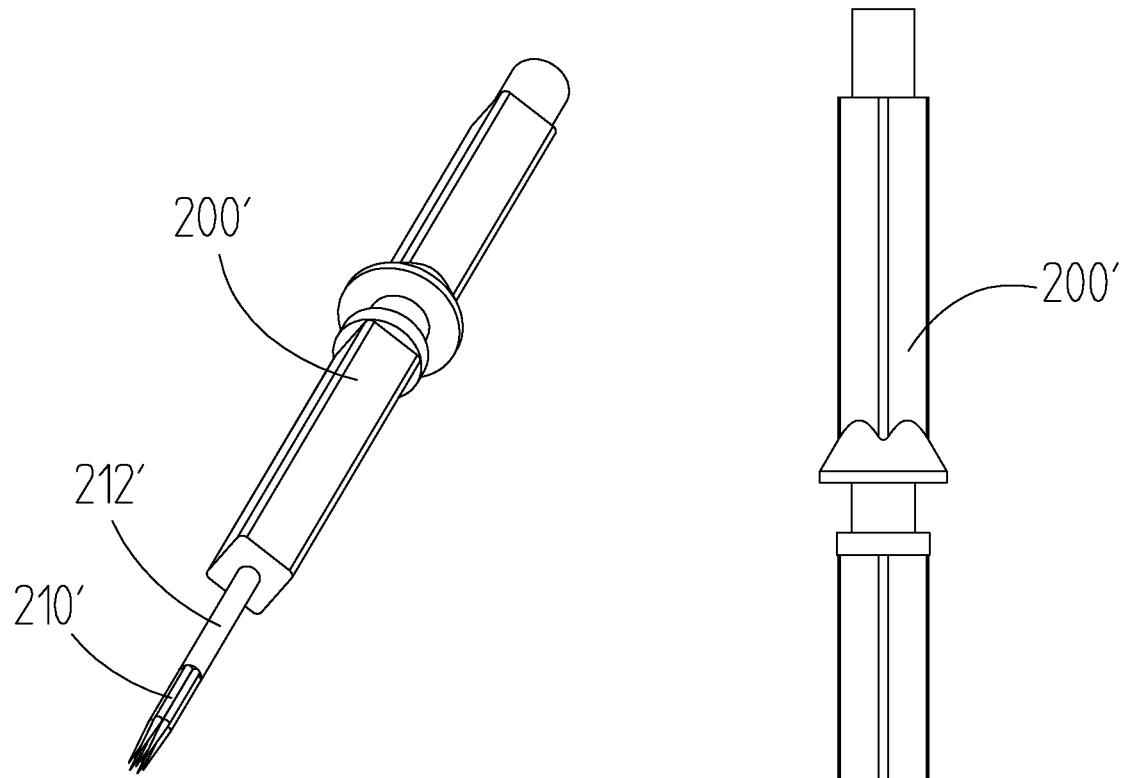
FIGS. 13A, 13B, and 13C are perspective, bottom, and side views, respectively, of the needle bundle of the needle assembly of FIG. 11A.
Figure 13B:
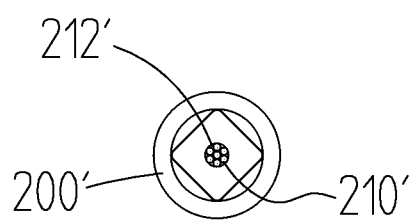
Figure 13C:
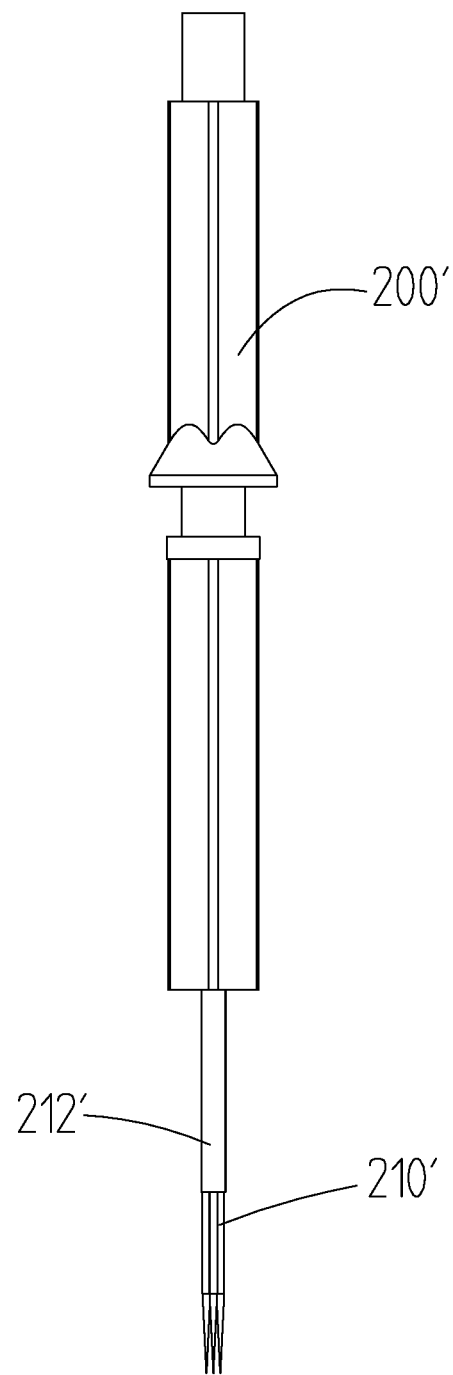
Figure 14A:
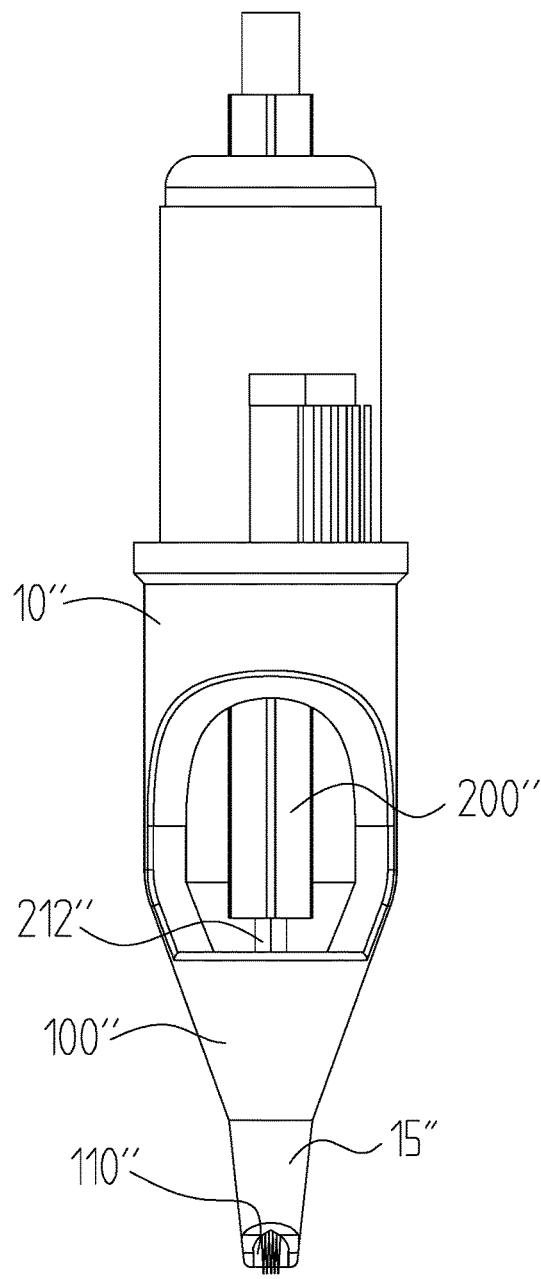
FIGS. 14A, 14B, and 14C are side, bottom, and perspective views of another needle assembly, according to another embodiment of the present disclosure.
Figure 14B:
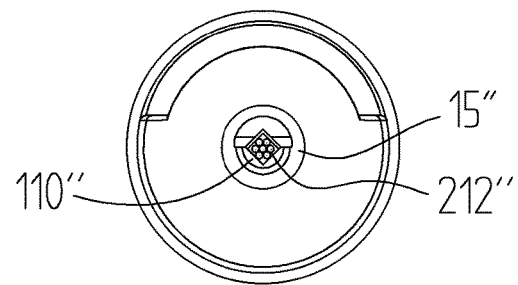
Figure 14C:
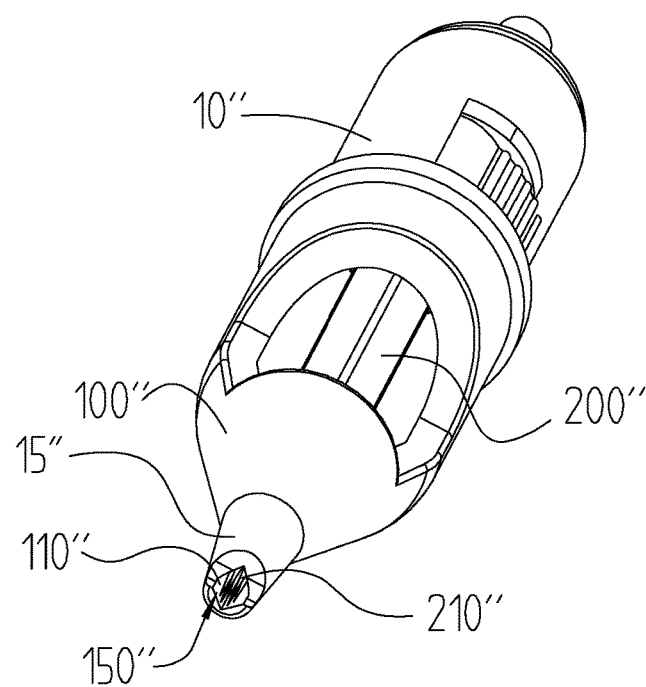
Figure 15A:
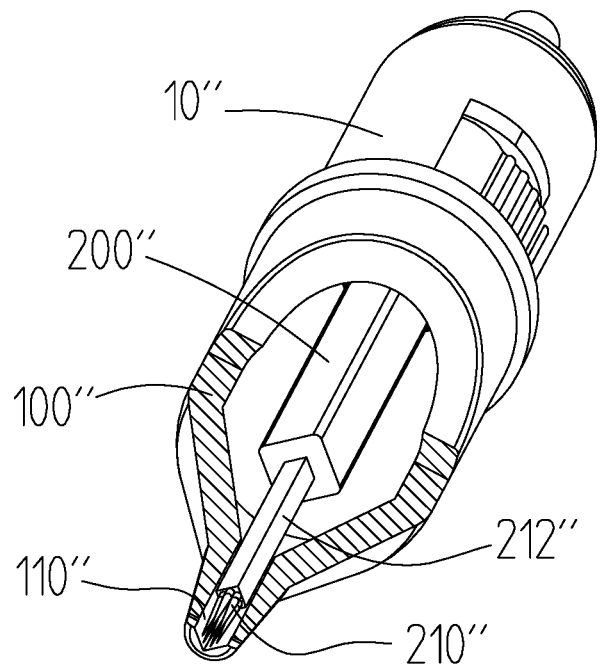
FIG. 15A is a (partially-cross-sectional) perspective view of the needle assembly of FIG. 14A.
Figure 15B:
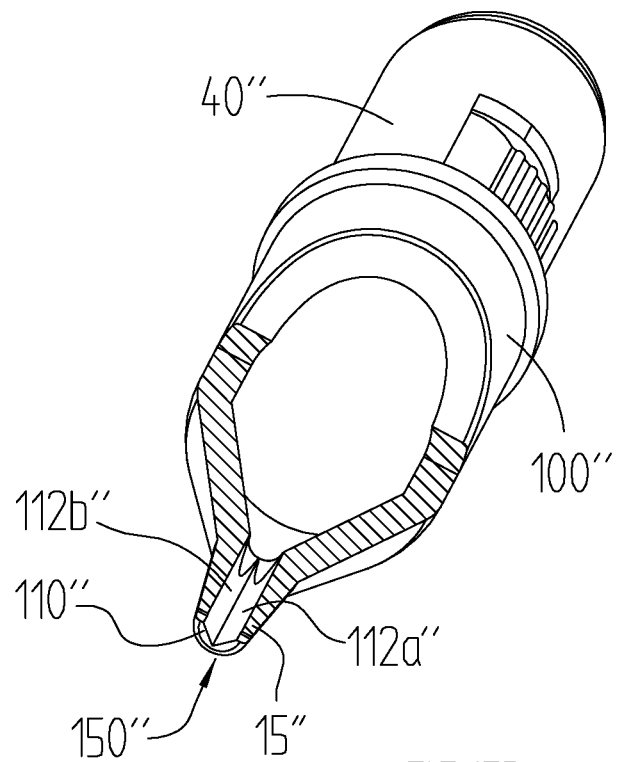
FIG. 15B is a partially-cutaway perspective view of the needle housing of the needle assembly of FIG. 14A.

As illustrated in FIG. 13A, the needles in needle set 210' are soldered together at a solder section 212', which has a generally circular cross-section. The solder material may be any suitable solder material such as lead-free tin solder. The needle set 210' is directly attached to the needle shaft, such as by adhesive bonding or inlay coupling. A connecting member, such as the connecting rod 215, is not required in this case to attach the needle set 210' to the needle shaft.

In conventional needle assemblies for round needles, the mouth opening is generally circular/round, and in conventional needle assemblies for flat needles, the mouth opening is generally rectangular, so that the mouth openings match the shapes the needle set. Due to various factors such as manufacturing tolerance in the diameter of the steel needles, in the spacing and positions of the needles in a needle set, and in the thickness and uniformity of the solder layer in the needle set, the actual cross-sectional shape and size of the needle set typically deviates from the nominal (stated or theoretical) shape and size, sometimes by a relatively large amount. In order to ensure that needle sets with variable sizes can be accommodated with the same needle mouthpiece and still allow the needles to smoothly reciprocate at the speed required for tattooing in the mouth opening, the mouth opening is typically sized so that a gap is always present between any needle set to be used and the inner wall of the mouthpiece to avoid jamming of the needles at the mouth opening. The gap is also typically sufficiently wide to allow ink flow between the needles and the mouthpiece through the mouth opening. However, as discussed earlier, such a large gap allow the needle tips to wobble. Even when the needles are pressed against the circular inner wall of the mouthpiece, the needles can still wobble sideways along the inner wall surface.

By comparison, in an embodiment described above, the mouth opening 150' can be relatively large and wobbling of the needles are still significantly reduced. The needles can thus be more precisely positioned for tattooing, without the downside of restricting the size of the mouth opening 150'.

FIGS. 14A-16C illustrate a needle assembly 10" for a round needle set, according to a further embodiment. Needle assembly 10" differs from the other embodiments described above in that a front/lower slider is provided on the needle bundle 200" by a bar 212" formed of a solder material on the needle set 210", and a front/lower stabilizer is provided in the mouth 15" of the housing body 100" of the housing 40". As illustrated, the bar 212" of the needle set 210" is formed around the needles and is shaped into a generally square bar. The bar 212" has a convex V-shaped edge providing two intersecting V-shaped sliding surfaces 260a", 260b". The mouth 15" has a mouth opening 150" and a V-shaped bore 110' at the narrowed beak section of the mouth 15", providing two guiding surfaces 112a", 112b".

As better seen in FIGS. 16A, 16B, and 16C, the needle set 210" of the needle bundle 200" may have a round formation of seven needles. The bar 212" may be formed of the same solder material that is used to solder the needles together as in a conventional needle set, but the solder material, with an optional filler material, is also used to provide the square-shaped slider bar, which is different from the round shape of the solder material on conventional soldered needle sets for round needles.

The beak section of the mouth with the V-shaped bore 110" provides a stabilizer that supports and guides the needle set 210". The V-shaped sliding surfaces 260a", 260b" conform to and mate with the V-shaped guiding surfaces 112a", 112b" and can slide on the guiding surfaces 112a", 112b" while maintaining contact. The V-shaped slider on bar 212" and the V-shaped bore 110" thus form a V-V sliding pair.

As depicted, the intersecting angle of the V-V sliding pair may be 90 degrees or may be another suitable angle.

The bar 212" may be formed and shaped by molding in a mold. The mold may be formed a material that does not tend to bond with or be adhered to the solder/filler material that is used to solder the needles and form the bar 212". For example, the mold may be formed from glass fibre and an adhesive epoxy resin. For example, such materials used in the electronics industry may be suitable, including the materials used to form glass fibre printed circuit board (PCB) substrate, epoxy board, glass fibre board, flame retardant (FR) glass-reinforced epoxy laminate materials such as FR-4 glass epoxy, fibre board, or the like. The selected mold material should be able to withstand the soldering temperature at which the selected solder becomes a molten material, and also does not bond to the solder material so it is easy to remove the molded bar and needle set from the mold after molding and provide relatively smooth surfaces on the bar 212".

A mold formed of such a material can be used in combination with known technology to form a round needle set with the bar 212" providing the convex V-shaped intersecting sliding surfaces. Alternatively, an existing round needle may be further processed to add filler or solder materials to form the convex V-shaped intersecting sliding surfaces.

The material for soldering and forming the bar 212" may be a solder material such as a tin-based solder material, or another suitable material, such as a plastic, a resin, or the like.

It should be understood that, in some embodiments, the needle bundle may be driven differently from the manner in the embodiments described above. For example, the drive shaft of the tattoo machine may extend into the needle housing to contact and drive the needle shaft.

Alternatively, the needle shaft may be fully enclosed in the needle housing and the drive shaft of the tattoo machine can drive the needle shaft without direct contact, such as by magnetic coupling. In such a case, the cap of the needle housing does not need to have a through bore (such as bore 450). An example of magnetically driving the needle bundle is disclosed in U.S. Ser. No. 11/040,185B2. When the needle bundle is magnetically driven, the needle bundle may be conveniently pulled back using an opposite magnetic force as well. Thus, it is not necessary to provide a biasing member to apply a longitudinal retraction force to pull the needle bundle from the extended position to the retracted position, although such a biasing member may still be useful. However, even in such a case, a biasing member that applies a radial or lateral biasing force to keep the sliding pair(s) engaged is still necessary in embodiments disclosed herein.

In an embodiment as described above, the lower end 310 of the biasing member 300 forms a fluid seal around the neck 234 of the needle shaft 220. The upper end 320 of the biasing member 300 can also closely fit around the inner wall of the body portion 100 of the needle housing 40, so the upper end portion 320 and the needle housing 40 also form a seal. The tubular stretchable section 330 is circumferentially closed. Thus, the biasing member 300 provides seals that prevent liquids, such as ink or blood that entered the needle housing 40 through the mouth opening 150, from flowing into the bore 450 of the cap 400. As a result, the biasing member 300 can also function as a seal.

In some embodiments, the upper end of the needle housing may have a closed end and the cap does not have a through bore as discussed above. In such embodiments, the biasing member does not need to provide any seal as the cap may provide a seal for preventing fluid contamination of the needle handle or tattoo machine.

To recap, an embodiment disclosed herein provides a needle assembly for a tattoo device, including a needle housing, a needle bundle, and a biasing member. The needle housing includes a body portion and a mouthpiece arranged at one end of the body portion, the body portion comprises a longitudinal channel, and the mouthpiece comprises a needle opening. A guiding and supporting member is provided on an inner wall of the needle housing, the guiding and supporting member having two guide surfaces. The needle bundle is movably mounted in the longitudinal channel and reciprocatively movable longitudinally between a retracted position and an extended position. The needle bundle comprises a needle shaft and a set of needles attached to the needle shaft. When the needle bundle is in the extended position, the needle set protrudes from the needle opening, and the needle shaft is biased by the biasing member to drive the needle bundle longitudinally back to the retracted position. The guide surfaces are parallel to a longitudinal movement direction of the needle bundle, and the two guide surfaces or their extension planes intersect. The biasing member is configured to apply a radial force to radially bias the needle bundle towards the intersection of the guide surfaces. The needle bundle comprises sliding surfaces respectively conforming to the two guide surfaces, respectively. The radial force applied by the biasing member biases the sliding surfaces of the needle bundle to slidably contact and engage the respective guide surfaces on the housing to form a V-V sliding pair, which maintains the sliding engagement during reciprocal movement of the needle bundle between the retracted position and the extended position.

The sliding surfaces on the needle bundle can be located at the lower (front) end portion, the middle portion, or the upper (rear) end portion of the needle bundle. For example, sliding surfaces may be provided on the needle set of the needle bundle, such as by solder filling, or on the needle shaft, such as by injection molding. The guide surfaces in the needle housing may be located at the lower (front) end portion, the middle portion, or the upper (rear) end portion of the needle housing. For example, the guide surfaces may be formed on a guiding and supporting member at the needle mouth opening, or the inner wall of the body portion, or the central bore of the cap.

As already illustrated above, the V-shaped intersection between the two guide surfaces of the needle housing, or the two sliding surfaces of the needle bundle, is not necessarily formed by an actual intersection of the two surfaces but can be formed by their respective extended planes. The intersecting angle of the two intersecting surfaces may also vary, such as in the range from 30 degrees to 150 degrees, or from 60 degrees to 120 degrees.

In some embodiments, one or more V-V sliding pairs may be formed between the needle bundle and the needle housing. For example, V-V sliding pairs may be provided on both the upper and lower sides of a contact point (e.g., the neck 234 in needle assembly 10) between the needle bundle and the biasing member, where the biasing member engages the needle bundle and applies the lateral biasing force to the needle bundle.

In some embodiments, more than two sliding pairs may be provided to further improve stability of the needles. For example, three sliding pairs may be provided, one located at the cap of the needle housing, one at the middle section of the housing body, and one located at the mouth of the needle housing.

In some embodiments, multiple different types of sliding pairs may be formed between the needle bundle and the needle housing. For example, the sliding pairs may include a V-V sliding pair and another type of sliding pair, which may be formed by a cylindrical rod in a circular bore or a square bar in a square bore. The rod/bar and the bore may also have other cross-sectional shapes. In such embodiments, the sliding pair closest to the mouth of the housing may be a V-V sliding pair and one or two other types of sliding pairs may be located closer to the rear end of the needle housing.

In an embodiment where a single sliding pair is provided to guide the needle bundle, the sliding pair should be V-shaped and located adjacent or close to the tip portion of the needles and the mouth of the housing, to provide more stability for the needle tip portion and thus more precise control of the position of the needle tip portion, as compared to positioning the sliding pair away from the mouth.

Example embodiments of the present disclosure includes:

Embodiment 1

A needle assembly for a tattoo device, characterized by comprising a needle housing (40, 40', 40"), a needle bundle (200, 200', 200") and a biasing member (300), wherein the needle housing (40, 40', 40") includes a body portion (100, 100', 100") and a mouthpiece (15, 15', 15") arranged at one end of the body portion (100, 100', 100"), the body portion (100, 100', 100") comprises a longitudinal channel (120), and the mouthpiece (15, 15', 15") comprises a needle opening (150, 150', 150"); at least one guiding and supporting member (110, 110B, 110C, 110D, 110E, 110F, 110', 110", 410) provided on an inner wall of the needle housing (40, 40', 40"), the guiding and supporting member (110, 110B, 110C, 110D, 110E, 110F, 110', 110", 410) having two guide surfaces (112a/112b, 112a'/112b', 112a"/112b", 412a/412b, 412a'/412b'); the needle bundle (200, 200', 200") movably mounted in the longitudinal channel (120) and reciprocatively movable longitudinally between a retracted position and an extended position; the needle bundle (200, 200', 200") comprising a needle shaft (220, 220B, 220C, 220D, 220E, 220F) and a plurality of needles (210, 210', 210") attached to the needle shaft (220, 220B, 220C, 220D, 220E, 220F); the needle bundle (200, 200', 200") comprising sliding surfaces (260a/260b, 260a"/260b", 240a/240b) respectively conforming to the two guide surfaces (112a/112b, 112a'/112b', 112a"/112b", 412a/412b, 412a'/412b'), respectively; wherein when the needle bundle (200, 200', 200") is in the extended position, the plurality of needles (210, 210', 210") protrudes from the needle opening (150, 150', 150"), and an end of the needle shaft (220, 220B, 220C, 220D, 220E, 220F) remote from the plurality of needles (210, 210', 210") is biased to drive the needle bundle longitudinally (200, 200', 200"); the biasing member (300) configured to apply a lateral force to laterally bias the needle bundle (200, 200', 200") towards the guide surfaces (112a/112b, 112a'/112b', 112a"/112b", 412a/412b, 412a'/412b'); the guide surfaces (112a/112b, 112a'/112b', 112a"/1.12b", 412a/412b, 412a'/412b') being parallel to a longitudinal movement direction of the needle bundle (200, 200', 200"), and the two guide surfaces (112a/112b, 112a'/112b', 112a"/112b", 412a/412b, 412a'/412b') or their extension planes intersect; the lateral force applied by the biasing member (300) biases the sliding surfaces (260a/260b, 260a"/260b", 240a/240b) of the needle bundle (200, 200', 200") to slidably contact the respective two guide surfaces (112a/112b, 112a'/112b', 112a"/112b", 412a/412b, 4120 of the needle housing (40, 40', 40")/412b').

Embodiment 2

The needle assembly of Embodiment 1, wherein the needle housing (40, 40', 40") also includes a cap (400, 400') at an end of the body portion ((100, 100', 100") remote from the mouthpiece (15, 15', 15"), the cap (400, 400') comprising a central through hole (450), the longitudinal channel (120) connecting the needle opening (150, 150', 150") and the central through hole (450); wherein when the needle bundle (200, 200', 200") is in the extended position, the end of the needle shaft (220, 220B, 220C, 220D, 220E, 220F) remote from the plurality of needles (210, 210', 210") is located in the central through hole (450); the biasing member (300) being configured to apply a longitudinal force to drive the needle bundle (200, 200', 200") longitudinally towards the retracted position.

Embodiment 3

The needle assembly of Embodiment 1 or 2, wherein the two guide surfaces (112a/112b, 112a'/112b', 112a"/112b", 412a/412b, 412a'/412b') intersect at an angle of 60 to 120 degrees to form a V shape.

Embodiment 4

The needle assembly of any of Embodiments 1 to 3, wherein the extension planes of the two guide surfaces (112a/112b, 112a'/112b', 12a"/112b", 412a/412b, 412a'/412b') intersect, and the two guide surfaces form a / \ or \ /shape.

Embodiment 5

The needle assembly of any of Embodiments 1 to 4, wherein a portion of the needle bundle (200, 200', 200") on the sliding surfaces (260a/260b, 260a"/260b", 240a/240b) has a quadrilateral, pentagonal, or hexagonal cross-section; the two sliding surfaces (260a/260b, 260a"/260b", 240a/240b) or their extension planes intersect, the direction of the lateral force points to the line at the intersection of the two sliding surfaces (260a/260b, 260a"/260b", 240a/240b) or their extensions.

Embodiment 6

The needle assembly of any of Embodiments 1 to 5, wherein the sliding surfaces (260a/260b, 260a"/260b", 240a/240b) are on the needle shaft (220).

Embodiment 7

The needle assembly of any of Embodiments 1 to 6, wherein the guide surfaces (112a/112b, 112a'/112b', 112a"/112b", 412a/412b, 412a'/412b') and the sliding surface (260a/260b, 260a"/260b", 240a/240b) form a V-V sliding pair, wherein the sliding surfaces (260a/260b, 260a''/260b'', 240a/240b) are at an end of the needle shaft (220) adjacent to the plurality of needles (210, 210', 210'').

Embodiment 8

The needle assembly of Embodiment 2, wherein the guiding and supporting members (110, 110B, 110C, 110D, 110E, 110F, 110', 110'', 410) are arranged on the cap (400, 400').

Embodiment 9

The needle assembly of any of Embodiments 1 to 8, wherein the guiding and supporting members (110, 110B, 110C, 110D, 110E, 110F, 110', 110'', 410) are arranged at the mouthpiece (15, 15', 15'').

Embodiment 10

The needle assembly of Embodiment 9, wherein the plurality of needles (210, 210', 210'') comprises an array of needles soldered together by a solder (212, 212', 212''), the array of needles and the solder (212, 212', 212'') are configured to conform to the guide surfaces (112a/112b, 112a'/112b', 112a''/112b'', 412a/412b, 412a'/412b'), so as to form the sliding surfaces (260a/260b, 260a''/260b'', 240a/240b).

Embodiment 11

The needle assembly of any of Embodiments 1 to 10, wherein the needle shaft (220, 220B, 220C, 220D, 220E, 220F) comprises a neck (234) for attaching the biasing member (300) thereto, the guiding and supporting member (110, 110B, 110C, 110D, 110E, 110F, 110', 110'', 410) comprises two guiding and supporting members (110, 110B, 110C, 110D, 110E, 110F, 110', 110'', 410) respectively located on two sides of the neck (234) so as to share the lateral force.

Embodiment 12

The needle assembly of any of Embodiments 1 to 11, wherein the guiding and supporting member (110, 110B, 110C, 110D, 110E, 110F, 110', 110'', 410) comprises two guiding surfaces (112a/112b, 112a'/112b', 112a''/112b'', 412a/412b, 412a'/412b') forming a ∧-shaped ridge, the needle bundle (200, 200', 200'') comprises two sliding surfaces (260a/260b, 260a''/260b'', 240a/240b) forming a V-shaped valley conforming to the ∧-shaped ridge.

It should be understood that the term "tattoo" as used herein may refer to cosmetic tattoos or permanent makeup, and tattoo equipment or machines may refer to equipment or machines for applying cosmetic tattoos or permanent makeup.

In this disclosure, a "V-shaped" profile formed by two surfaces, for example, of a guideway or slider, may be generally V-shaped and is not limited to the geometric V shape. For example, the guide surfaces forming the V-shaped guideway do not have to be perfectly flat and directly intersect each other as long as the V-shaped guideway provides the balancing reactive forces to stabilize the needle bundle in all lateral directions (including radial and circumferential directions) as described herein.

It should also be understood that modifications and variations to the specific embodiments described above are possible.

As can be appreciated, a needle assembly described herein may be used or adapted to apply other types of liquids to skin. For example, the applied liquid may include coloured liquids or pigments, or may include a medicinal or therapeutic agent, collagen, or other like or similar substances. The needle assembly may be used in a liquid applicator for applying the selected liquid.

Other features, modifications, and applications of the embodiments described here may be understood by those skilled in the art in view of the disclosure herein.

CONCLUDING REMARKS

It will be understood that any range of values herein is intended to specifically include any intermediate value or sub-range within the given range, and all such intermediate values and sub-ranges are individually and specifically disclosed.

It will also be understood that the word "a" or "an" is intended to mean "one or more" or "at least one", and any singular form is intended to include plurals herein.

It will be further understood that the term "comprise", including any variation thereof, is intended to be open-ended and means "include, but not limited to," unless otherwise specifically indicated to the contrary.

When a list of items is given herein with an "or" before the last item, any one of the listed items or any suitable combination of two or more of the listed items may be selected and used.

Of course, the above described embodiments of the present disclosure are intended to be illustrative only and in no way limiting. The described embodiments are susceptible to many modifications of form, arrangement of parts, details, and order of operation. The invention, rather, is intended to encompass all such modification within its scope, as defined by the claims.

What is claimed is:

1. A needle assembly for a tattoo device, comprising:
   a housing comprising a longitudinal channel and a pair of first and second guide surfaces forming a V-shaped guideway on an inner wall of the housing;
   a needle bundle mounted in the longitudinal channel and reciprocally movable between a retracted position and an extended position, the needle bundle comprising a pair of first and second sliding surfaces for slidably engaging the guideway;
   a biasing member engaged with the housing and the needle bundle for biasing the needle bundle at least radially to slidably engage the guideway such that the pair of first and second guide surfaces of the guideway and the pair of first and second sliding surfaces of the needle bundle form a V-V sliding pair and maintain sliding engagement during reciprocal movement of the needle bundle between the retracted position and the extended position.

2. The needle assembly of claim 1, wherein the housing comprises a front end and a rear end, the front end comprising a mouthpiece having a mouth opening, the longitudinal channel extending from the front end to the rear end, and wherein the V-V sliding pair is located adjacent to or in the mouthpiece.

3. The needle assembly of claim 2, wherein the housing and the needle bundle are configured to form one or more further sliding pairs, a first one of the one or more further sliding pairs being located adjacent to or at the rear end of the housing.

4. The needle assembly of claim 3, wherein the first one of the one or more further sliding pairs comprises a further V-V sliding pair.

5. The needle assembly of claim 4, wherein the housing comprises a cap at the rear end of the housing, the cap comprising a bore having a pair of third and fourth guide surfaces forming a further V-shaped guideway in the cap, and the needle bundle comprises a corresponding pair of third and fourth sliding surfaces adjacent to the cap for slidably engaging the further V-shaped guideway in the cap to form the further V-V sliding pair.

6. The needle assembly of claim 2, wherein the mouthpiece comprises the pair of first and second guide surfaces.

7. The needle assembly of claim 1, wherein the housing comprises a M-shaped member on the inner wall, the M-shaped member comprising the pair of first and second guide surfaces.

8. The needle assembly of claim 1, wherein the needle bundle comprises a needle shaft and a set of needles attached to the needle shaft, and the needle shaft comprises the pair of first and second sliding surfaces.

9. The needle assembly of claim 1, wherein the needle bundle comprises a needle shaft and a set of needles soldered together by a solder bar attached to the needle shaft, and the solder bar comprises the pair of first and second sliding surfaces.

10. The needle assembly of claim 1, wherein the biasing member is further configured to apply a longitudinal force to longitudinally bias the needle bundle from the extended position towards the retracted position.

11. The needle assembly of claim 1, wherein the pair of first and second guide surfaces and the pair of first and second sliding surfaces are parallel to a longitudinal movement direction of the needle bundle.

12. The needle assembly of claim 1, wherein the pair of first and second guide surfaces, or the respective extension planes of the pair of first and second guide surfaces, intersect at an angle of 60 to 120 degrees.

13. The needle assembly of claim 1, wherein the needle bundle comprises a neck for engaging a front end of the biasing member, a first sliding pair is provided between the neck and a front end of the needle bundle, and a second sliding pair is provided between the neck and a rear end of the needle bundle, at least one of the first sliding pair and the second sliding pair comprising the V-V sliding pair.

14. The needle assembly of claim 1, wherein the biasing member is oriented to generate a radial biasing force directed towards an intersection of the pair of first and second guide surfaces.

15. The needle assembly of claim 1, wherein at least one of the pair of first and second guide surfaces and the pair of first and second sliding surfaces is lubricated by a lubricant or has a lubricated coating.

16. The needle assembly of claim 1, wherein at least one of the pair of first and second guide surfaces and the pair of first and second sliding surfaces comprises polyoxymethylene or polytetrafluoroethylene.

17. A needle assembly for a tattoo device, comprising:
- a housing comprising a longitudinal channel and a V-shaped guideway extending longitudinally in the longitudinal channel;
- a needle bundle mounted in the longitudinal channel and reciprocally movable between a retracted position and an extended position, the needle bundle comprising a V-shaped slider for slidably engaging the guideway; and
- a biasing member for radially biasing the V-shaped slider of the needle bundle to slidably engage the V-shaped guideway during movement of the needle bundle between the retracted and extended positions, such that the V-shaped guideway and the V-shaped slider maintain sliding engagement during the movement of the needle bundle between the retracted and extended positions.

18. The needle assembly of claim 17, wherein the guideway and the slider form a V-V sliding pair.

19. The needle assembly of claim 18, wherein the guideway is concave V-shaped and the slider is convex V-shaped.

20. The needle assembly of claim 18, wherein the guideway is convex V-shaped and the slider is concave V-shaped.

* * * * *